United States Patent [19]
Fischer et al.

[11] Patent Number: 5,972,995
[45] Date of Patent: Oct. 26, 1999

[54] COMPOSITIONS AND METHODS FOR CYSTIC FIBROSIS THERAPY

[75] Inventors: Horst Bernhard Fischer; Beate Illek, both of Albany, Calif.

[73] Assignee: Children's Hospital Medical Center of Northern California, Oakland, Calif.

[21] Appl. No.: 08/951,912

[22] Filed: Oct. 16, 1997

[51] Int. Cl.$^6$ .......................... A61K 31/35; A61K 31/21
[52] U.S. Cl. .......................... 514/456; 514/513; 514/851
[58] Field of Search .................................. 514/456, 851, 514/513

[56] References Cited

U.S. PATENT DOCUMENTS

| | | | |
|---|---|---|---|
| 5,639,661 | 6/1997 | Welsh et al. | 435/252.3 |
| 5,650,433 | 7/1997 | Watanabe et al. | 514/456 |
| 5,733,926 | 3/1998 | Gorbach | 514/456 |
| 5,756,538 | 5/1998 | Cassels et al. | 514/456 |

FOREIGN PATENT DOCUMENTS

| | | |
|---|---|---|
| 62-105816 | 3/1987 | Japan . |
| 5-330545 | 9/1993 | Japan . |
| 6-277493 | 2/1994 | Japan . |
| 7-135875 | 3/1995 | Japan . |

OTHER PUBLICATIONS

Brown et al., "Chemical chaperones correct the mutant phenotype of the ΔF508 cystic fibrosis transmembrane conductance regulatory protein," *Cell Stress & Chaperones* 1(2): 117–125, 1996.

Hwang et al., "Genistein potentiates wild-type and ΔF508-CFTR channel activity," *American Journal of Physiology* 273(3, part 1): C988–C–998, 1997.

Scott and Cooperstein, "Ascorbic acid stimulates chloride transport in the amphilbian cornea," *Investigative Ophtalmology* 14(10): 763–766, 1975.

Smith, "Treatment of cystic fibrosis based on understanding CFTR," *J. Inher. Metab. Dis* 18:508–516, 1995.

Rubenstein et al., "In Vitro Pharmacologic Restoration of CFTR-mediated Chloride Transport with Sodium 4-Phenylbutyrate in Cystic Fibrosis Epithelial Cells," *J. Clin. Invest.* 100(10): 2457–2465, 1997.

Sheppard et al., "Mutations in CFTR associated with mild-disease-form CI channels with altered pore properties," *Nature* 362: 160–164, 1993.

Anderson, et al., "Generation of cAMP-Activated Chloride Currents by Expression of CFTR," *Science* 251:679–682, 1991.

Knowles et al., "In Vivo Nasal Potential Difference: Techniques and Protocols for Assessing Efficacy of Gene Transfer in Cystic Fibrosis," *Human Gene Therapy* 6: 445–455, 1995.

Riordan et al., "Identification of the Cystic Fibrosis Gene: Cloning and Characterization of Complementary DNA," *Science* 245: 1066–1073, 1989.

Illek et al., "cAMP-independent activation of CFTR C1 channels by the tyrosine kinase inhibitor genistein," *Cell Physiol.* 37: C886–C893, 1995.

*Primary Examiner*—Kevin E. Weddington
*Attorney, Agent, or Firm*—Seed and Berry LLP

[57] ABSTRACT

Compositions and methods for therapy of cystic fibrosis and other conditions are provided. The compositions comprise one or more flavones and/or isoflavones capable of stimulating chloride transport in epithelial tissues. Therapeutic methods involve the administration (e.g., orally or via inhalation) of such compositions to a patient afflicted with cystic fibrosis and/or another condition responsive to stimulation of chloride transport.

22 Claims, 9 Drawing Sheets

COMPOSITIONS AND METHODS FOR CYSTIC FIBROSIS THERAPY

TECHNICAL FIELD

The present invention relates generally to the treatment of cystic fibrosis. The invention is more particularly related to compositions comprising one or more flavones and/or isoflavones, which may be used to activate chloride transport (ie., absorption and/or secretion) in epithelial tissues of the airways, the intestine, the pancreas and other exocrine glands, and for cystic fibrosis therapy.

BACKGROUND OF THE INVENTION

Cystic fibrosis is a lethal genetic disease afflicting approximately 30,000 individuals in the United States. Approximately 1 in 2500 caucasians is born with the disease, making it the most common lethal, recessively inherited disease in that population.

Cystic fibrosis affects the secretory epithelia of a variety of tissues, altering the transport of water, salt and other solutes into and out of the blood stream. In particular, the ability of epithelial cells in the airways, pancreas and other tissues to transport chloride ions, and accompanying sodium and water, is severely reduced in cystic fibrosis patients, resulting in respiratory, pancreatic and intestinal ailments. The principle clinical manifestation of cystic fibrosis is the resulting respiratory disease, characterized by airway obstruction due to the presence of a thick mucus that is difficult to clear from airway surfaces. This thickened airway liquid contributes to recurrent bacterial infections and progressively imparied respiration, eventually resulting in death.

In cystic fibrosis, defective chloride transport is generally due to a mutation in a chloride channel known as the cystic fibrosis transmembrane conductance regulator (CFTR; see Riordan et al., *Science* 245:1066–73, 1989). CFTR is a linear chloride channel found in the plasma membrane of certain epithelial cells, where it regulates the flow of chloride ions in response to phosphorylation by a cyclic AMP-dependent kinase. Many mutations of CFTR have been reported, the most common of which is a deletion of phenylalanine at position 508 (ΔF508-CFTR), which is present in approximately 70% of patients with cystic fibrosis. A glycine to aspartate substitution at position 551 (G55 ID-CFTR) occurs in approximately 1% of cystic fibrosis patients.

Current treatments for cystic fibrosis generally focus on controlling infection through antibiotic therapy and promoting mucus clearance by use of postural drainage and chest percussion. However, even with such treatments, frequent hospitalization is often required as the disease progresses. New therapies designed to increase chloride ion conductance in airway epithelial cells have been proposed, but their long term beneficial effects have not been established and such therapies are not presently available to patients.

Accordingly, improvements are needed in the treatment of cystic fibrosis. The present invention fulfills this need and further provides other related advantages.

SUMMARY OF THE INVENTION

Briefly stated, the present invention provides compositions and methods for the therapy of cystic fibrosis. Within one aspect, the present invention provides methods for enhancing chloride transport in epithelial cells, comprising contacting epithelial cells with a compound selected from the group consisting of flavones and isoflavones, wherein the compound is capable of stimulating chloride transport, and wherein the compound is not genistein. Within certain embodiments, the compound is quercetin, apigenin, kaempferol or biochanin A. For enhancing chloride transport in airway epithelial cells of a mammal, compounds may be administered orally or by inhalation.

Within other aspects, the present invention provides methods for treating cystic fibrosis in a patient, comprising administering a compound selected from the group consisting of flavones and isoflavones, wherein the compound is capable of stimulating chloride transport, and wherein the compound is not genistein. Within certain embodiments, the compound is quercetin, apigenin, kaempferol or biochanin A. Compounds may be administered orally or by inhalation.

Within further related aspects, the present invention provides methods for increasing chloride ion conductance in airway epithelial cells of a patient afflicted with cystic fibrosis, wherein the patient's CFTR protein has a deletion at position 508, the method comprising administering to a mammal one or more compounds selected from the group consisting of flavones and isoflavones, wherein the compound is capable of stimulating chloride secretion.

Within further aspects, pharmaceutical compositions for treatment of cystic fibrosis are provided, comprising one or more flavones or isoflavones capable of stimulating chloride transport in combination with a pharmaceutically acceptable carrier. Within certain embodiments, such compositions may comprise quercetin, apigenin, kaempferol and/or biochanin A in combination with a pharmaceutically acceptable carrier.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1:
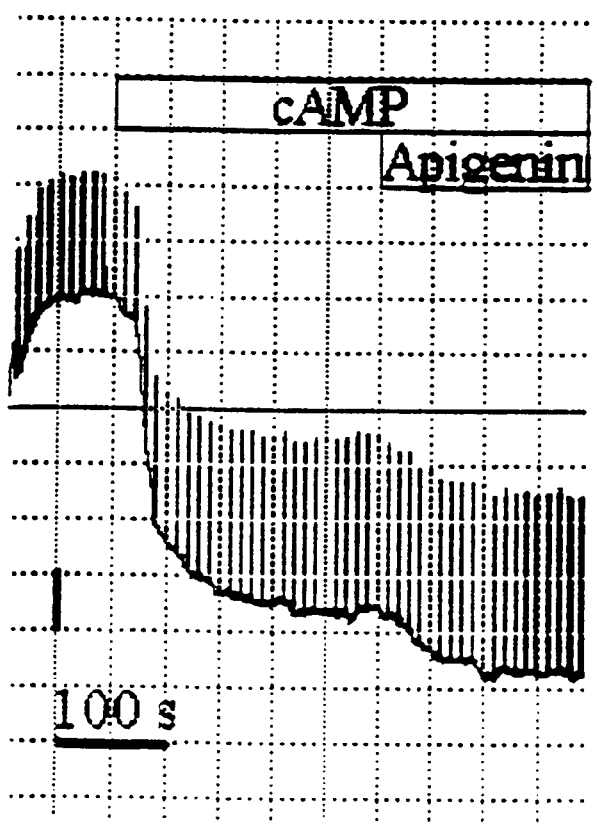
FIG. 1 is a recording of transepithelial short-circuit current (Y axis) as a function of time (X axis), showing the effect of apigenin on the current across a Calu-3 cell monolayer. Measurements were performed in an Ussing chamber, where the basolateral membrane was permeabilized with α-toxin and a chloride gradient was applied across the apical membrane as a driving force. Tissue was first stimulated with cAMP (100 µM). Apigenin (50 µM) was subsequently added as indicated. The horizontal bar represents 100 seconds, and the vertical bar represents 12 µA/cm².

As noted above, the present invention is generally directed to compositions and methods for the treatment of diseases characterized by defective chloride transport in epithelial tissues, including cystic fibrosis, and diseases with excessive accumulation of mucus, including cystic fibrosis, chronic bronchitis and asthma. It has been found, within the context of the present invention, that certain flavones and isoflavones are capable of stimulating chloride transport in epithelial tissues (e.g., tissues of the airways, intestine, pancreas and other exocrine glands) in a cyclic-AMP independent manner. Such therapeutic compounds may be administered to patients afflicted with cystic fibrosis as described herein.

The term "flavones", as used herein refers to a compound based on the core structure of flavone:

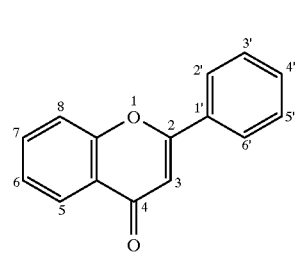

Flavone

An "isoflavone" is an isomer of a flavone (i.e., the phenyl moiety at position 2 is moved to position 3), and having the core structure shown below:

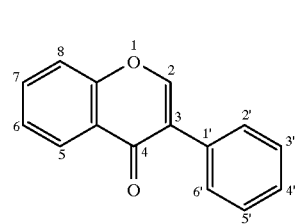

Isoflavone

Many flavones are naturally-occurring compounds, but synthetic flavones and isoflavones are also encompassed by the present invention. A flavone or isoflavone may be modified to comprise any of a variety of functional groups, such as hydroxyl and/or ether groups. Preferred flavones comprise one or more hydroxyl groups, such as the trihydroxyflavone apigenin, the tetrahydroxyflavone kaempferol and the pentahydroxyflavone quercetin. Preferred isoflavones comprise one or more hydroxyl and/or methoxy groups, such as the methoxy, dihydroxy isoflavone biochanin A.

Flavones and isoflavones for use within the context of the present invention have the ability to stimulate chloride transport in epithelial tissues. Such transport may result in secretion or absorption of chloride ions. The ability to stimulate chloride transport may be assessed using any of a variety of systems. For example, in vitro assays using a mammalian trachea or a cell line, such as the permanent airway cell line Calu-3 (ATCC Accession Number HTB55) may be employed. Alternatively, the ability to stimulate chloride transport may be evaluated within an in vivo assay employing a mammalian nasal epithelium. In general, the ability to stimulate chloride transport may be assessed by evaluating CFTR-mediated currents across a membrane by employing standard Ussing chamber (see Ussing and Zehrahn, Acta. Physiol Scand. 23:110–127, 1951) or nasal potential difference measurements (see Knowles et al., Hum. Gene Therapy 6:445–455, 1995). Within such assays, a flavone or isoflavone that stimulates a statistically significant increase in chloride transport at a concentration of about 1–300 μM is said to stimulate chloride transport.

Within one in vitro assay, the level of chloride transport may be evaluated using mammalian pulmonary cell lines, such as Calu-3 cells, or primary bovine tracheal cultures. In general, such assays employ cell monolayers, which may be prepared by standard cell culture techniques. Within such systems, CFTR-mediated chloride current may be monitored in an Ussing chamber using intact epithelia. Alternatively, chloride transport may be evaluated using epithelial tissue in which the basolateral membrane is permeabilized with Staphylococcus aureus α-toxin, and in which a chloride gradient is imposed across the apical membrane (see Illek et al., *Am. J. Physiol.* 270:C265–75, 1996). In either system, chloride transport is evaluated in the presence and absence of a test compound (i.e., a flavone or isoflavone), and those compounds that stimulate chloride transport as described above may be used within the methods provided herein.

Within another in vitro assay for evaluating chloride transport, cells are transfected with a chloride channel gene (e.g., CFTR) having a mutation associated with cystic fibrosis. Any CFTR gene that is altered relative to the normal human sequence provided in SEQ ID NO: 1, such that the encoded protein contains a mutation associated with cystic fibrosis, may be employed within such an assay. The most common disease-causing mutation in cystic fibrosis is a deletion of phenylalanine at position 508 in the CFTR protein (ΔF508-CFTR; SEQ ID NO:4). Accordingly, the use of a CFTR gene encoding ΔF508-CFTR is preferred. However, genes encoding other altered CFTR proteins (e.g., G551D-CFTR; SEQ ID NO:6) may also be used. Cells such as NIH 3T3 fibroblasts may be transfected with an altered CTFR gene, such as ΔF508-CFTR, using well known techniques (see Anderson et al., *Science* 25:679–682, 1991). The effect of a compound on chloride transport in such cells may be evaluated by monitoring CFTR-mediated currents using the patch clamp method (see Hamill et al., *Pflugers Arch.* 391:85–100, 1981) with and without compound application.

Within another in vitro assay, a mutant CFTR may be microinjected into cells such as Xenopus oocytes. Chloride conductance mediated by the CFTR mutant in the presence and absence of a test compound may be monitored with the two electrode voltage clamp method (see Miledi et al., *Proc. R. Soc. Lond. Biol.* 218:481–484, 1983).

Alternatively, such assays may be performed using a mammalian trachea, such as a primary cow tracheal epithelium using the Ussing chamber technique as described above. Such assays are performed in the presence and absence of test compound to identify flavone and isoflavones that stimulate chloride transport.

In vivo, chloride secretion may be assessed using measurements of nasal potential differences in a mammal, such as a human or a mouse. Such measurements may be performed on the inferior surface of the inferior turbinate following treatment of the mucosal surface with a test compound during perfusion with the sodium transport blocker amiloride in chloride-free solution. The nasal potential difference is measured as the electrical potential measured on the nasal mucosa with respect to a skin electrode placed on a slightly scratched skin part (see Alton et al., *Eur. Respir. J.* 3:922–926, 1990) or with respect to a subcutaneous needle (see Knowles et al., *Hum. Gene Therapy* 6:445–455, 1995). Nasal potential difference is evaluated in the presence and absence of test compound, and those compounds that results in a statistically significant increase in nasal potential difference stimulate chloride transport.

As noted above, any flavone or isoflavone that stimulates chloride transport within at least one of the above assays may be used for therapy of cystic fibrosis, other diseases characterized by abnormally high mucus accumulation in the airways or intestinal disorders such as constipation. Preferred therapeutic compounds include quercetin (3,3',4', 5,7-pentahydroxyflavone), apigenin (4'5,7-trihydroxy-flavone), kaempferol (3,4',5,7-tetrahydroxyflavone) and biochanin A (4'-methoxy-5,7-dihydroxyisoflavone), as depicted below:

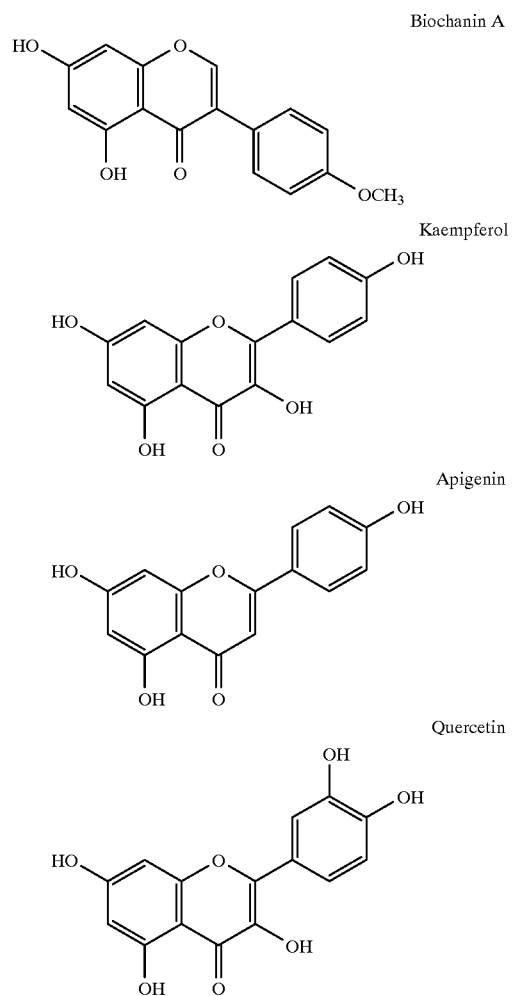

Other suitable therapeutic compounds may be identified using the representative assays as described herein.

Quercetin, apigenin, kaempferol, biochanin A and other flavones and isoflavones may generally be prepared using well known techniques, such as those described by Shakhova et al., *Zh. Obshch. Khim.* 32:390, 1962; Farooq et al., *Arch. Pharm.* 292:792, 1959; and Ichikawa et al., *Org. Prep. Prog. Int.* 14:183, 1981. Alternatively, such compounds may be commercially available (e.g., from Indofine Chemical Co., Inc., Somerville, N.J. or Sigma-Aldrich, St. Louis, Mo.). Further modifications to such compounds may be made using conventional organic chemistry techniques, which are well known to those of ordinary skill in the art.

For in vivo use, a therapeutic compound as described herein is generally incorporated into a pharmaceutical composition prior to administration. Within such compositions, one or more therapeutic compounds as described herein are present as active ingredient(s) (ie., are present at levels sufficient to provide a statistically significant effect on nasal potential difference, as measured using a representative assay as provided herein). A pharmaceutical composition comprises one or more such compounds in combination with any pharmaceutically acceptable carrier(s) known to those skilled in the art to be suitable for the particular mode of administration. In addition, other pharmaceutically active ingredients (including other therapeutic agents) may, but need not, be present within the composition.

Administration may be achieved by a variety of different routes. One preferred route is oral administration of a composition such as a pill, capsule or suspension. Such compositions may be prepared according to any method known in the art, and may comprise any of a variety of inactive ingredients. Suitable excipients for use within such compositions include inert diluents (which may be solid materials, aqueous solutions and/or oils) such as calcium or sodium carbonate, lactose, calcium or sodium phosphate, water, arachis oil, peanut oil liquid paraffin or olive oil; granulating and disintegrating agents such as maize starch, gelatin or acacia and/or lubricating agents such as magnesium stearate, stearic acid or talc. Other inactive ingredients that may, but need not, be present include one or more suspending agents (e.g., sodium carboxymethylcellulose, methylcellulose, hydroxypropylmethylcellulose, sodium alginate, polyvinylpyrrolidone, gum tragacanth and gum acacia), thickeners (e.g., beeswax, paraffin or cetyl alcohol), dispersing or wetting agents, preservatives (e.g., antioxidants such as ascorbic acid), coloring agents, sweetening agents and/or flavoring agents.

A pharmaceutical composition may be prepared with carriers that protect active ingredients against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Particularly preferred are methods in which the therapeutic compound(s) are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and to improve solubility.

Pharmaceutical compositions are administered in an amount, and with a frequency, that is effective to inhibit or alleviate the symptoms of cystic fibrosis and/or to delay the progression of the disease. The effect of a treatment may be clinically determined by nasal potential difference measurements as described herein. The precise dosage and duration of treatment may be determined empirically using known testing protocols or by testing the compositions in model systems known in the art and extrapolating therefrom. Dosages may also vary with the severity of the disease. A pharmaceutical composition is generally formulated and administered to exert a therapeutically useful effect while minimizing undesirable side effects. In general, an oral dose ranges from about 200 mg to about 1000 mg, which may be administered 1 to 3 times per day. Compositions administered as an aerosol are generally designed to provide a final concentration of about 10 to 50 $\mu$M at the airway surface, and may be administered 1 to 3 times per day. It will be apparent that, for any particular subject, specific dosage regimens may be adjusted over time according to the individual need.

As noted above, a pharmaceutical composition may be administered to a mammal to stimulate chloride transport, and to treat cystic fibrosis. Patients that may benefit from administration of a therapeutic compound as described herein are those afflicted with cystic fibrosis. Such patients may be identified based on standard criteria that are well known in the art, including the presence of abnormally high salt concentrations in the sweat test, the presence of high nasal potentials, or the presence of a cystic fibrosis-associated mutation. Activation of chloride transport may also be beneficial in other diseases that show abnormally high mucus accumulation in the airways, such as asthma and chronic bronchitis. Similarly, intestinal constipation may benefit from activation of chloride transport by a flavone or isoflavone as provided herein.

Summary of Sequence Listing

SEQ ID NO:1 is a DNA sequence encoding human CFTR.

SEQ ID NO:2 is an amino acid sequence of human CFTR.

SEQ ID NO:3 is a DNA sequence encoding human CFTR with the $\Delta$F508 mutation.

SEQ ID NO:4 is an amino acid sequence of human CFTR with the $\Delta$F508 mutation.

SEQ ID NO:5 is a DNA sequence encoding human CFTR with the G551D mutation.

SEQ ID NO:6 is an amino acid sequence of human CFTR with the G55ID mutation.

The following Examples are offered by way of illustration and not by way of limitation.

EXAMPLES

Example 1

Stimulation of Chloride Transport by Representative Flavones and Isoflavones in Airway Cells This Example illustrates the use of the representative compounds apigenin, quercetin and biochanin A to enhance chloride secretion in Calu-3 human pulmonary cultures or in primary bovine tracheal cultures.

A Calu-3 cell monolayer was prepared in an Ussing chamber as described by Illek et al., *Am. J. Physiol.* 270:C265–275, 1996. The basolateral membrane was permeabilized with $\alpha$-toxin and a chloride gradient was applied across the apical membrane as a driving force (see Illek et al, *Am. J. Physiol.* 2,70:C265–C275, 1996). The tissue was first stimulated with cAMP (100 $\mu$M), and then with a representative flavone or isoflavone.

Figure 2:
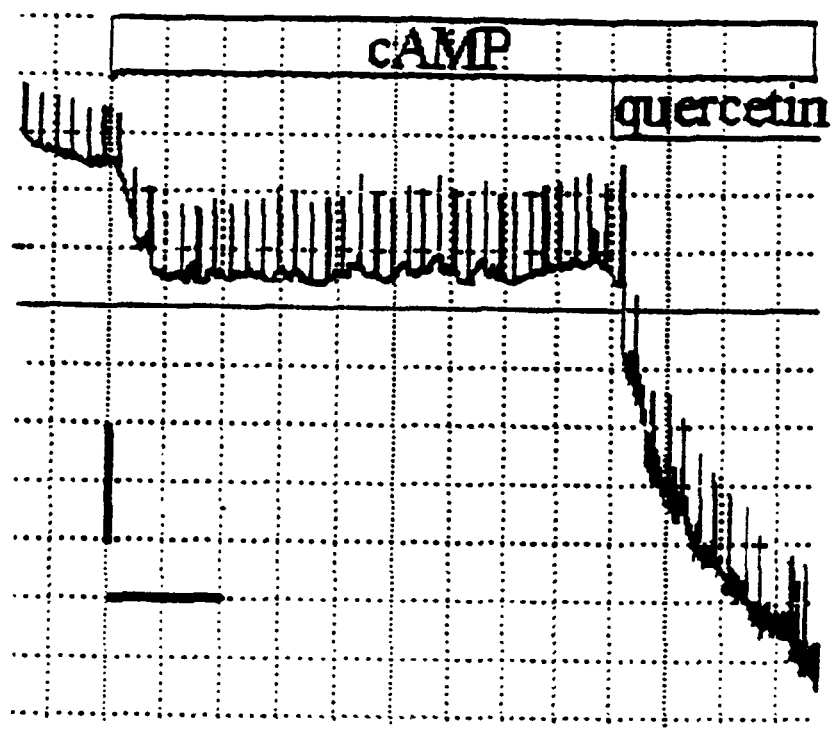
FIG. 2 is a recording showing the effect of quercetin on transepithelial short-circuit current across a Calu-3 cell monolayer in an Ussing chamber, where the basolateral membrane was permeabilized with α-toxin and a chloride gradient was applied across the apical membrane as a driving force. Tissue was first stimulated with cAMP (100 µM). Quercetin (30 µM) was subsequently added as indicated. Bars are 140 seconds (horizontal) and 12 µA/cm² (vertical).

As shown in FIGS. 1 and 2, subsequent addition of apigenin or quercetin further stimulated chloride current. FIG. 1 illustrates the short circuit current across the Calu-3 cell monolayer before and after addition of apigenin (50 $\mu$M). FIG. 2 illustrates the effect of quercetin (30 $\mu$M) on chloride current across a Calu-3 monolayer. In both cases, the flavone stimulated chloride current beyond the stimulation achieved by cAMP.

Figure 3:
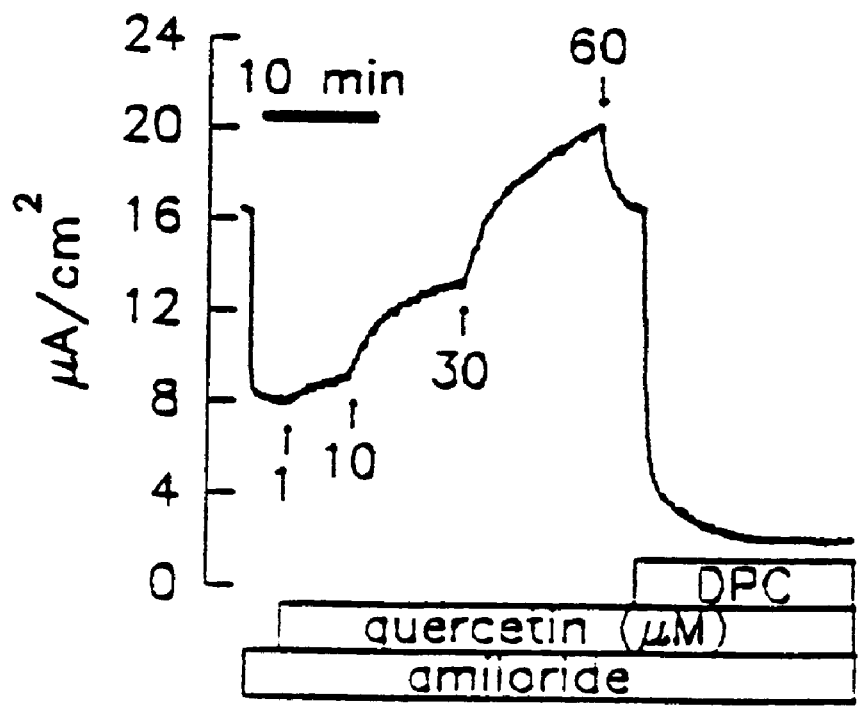
FIG. 3 is a recording illustrating the dose-dependent stimulation of transepithelial chloride secretion by quercetin (in the amounts indicated) across a primary bovine tracheal epithelium. Amiloride (50 µM) was added to block sodium transport as indicated. The CFTR channel blocker diphenylcarboxylate (DPC, 5 mM) was added as shown.

FIG. 3 illustrates the results of a related experiment to evaluate the dose-dependent stimulation of transepithelial chloride secretion by quercetin across a primary bovine tracheal epithelium. The epithelial cells were first treated with amiloride (50 $\mu$M), and then with quercetin at the indicated concentrations. The dose-response relation yielded a halfmaximal stimulation at 12.5 $\mu$M. At high concentrations of quercetin, the current was blocked. Current was fully inhibited by the CFTR channel blocker diphenylcarboxylate (DPC, 5 mM).

Figure 4:
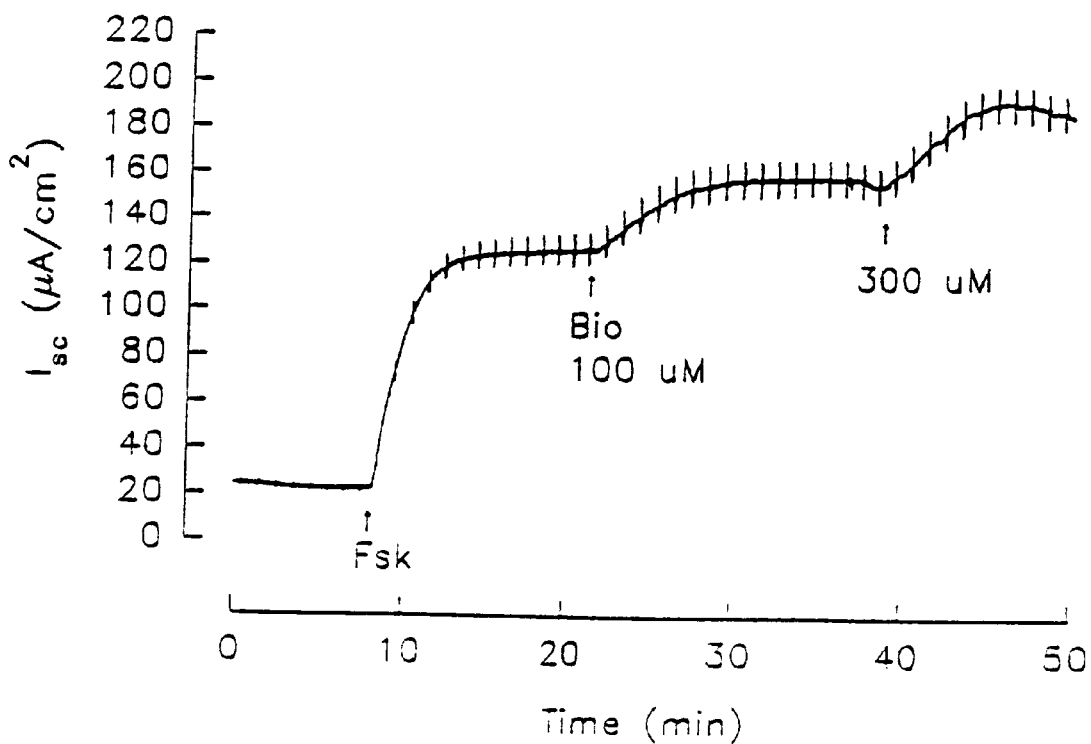
FIG. 4 is a recording showing the effect of biochanin A on transepithelial short-circuit current across a Calu-3 cell monolayer in an Ussing chamber, where the basolateral membrane was permeabilized with α-toxin and a chloride gradient was applied across the apical membrane as a driving force. The tissue was first stimulated with forskolin (Fsk, 10 μM). Subsequent addition of biochanin A (Bio, 100 and 300 μM) was subsequently added as indicated.

To evaluate the effect of biochanin A, a Calu-3 cell monolayer was prepared and permeabilized as described above. The tissue was first stimulated with with forskolin (Fsk, 10 μM). The effect of biochanin A (Bio, 100 and 300 μM) on short-circuit current ($I_{sc}$) across the Calu-3 monolayer was evaluated in an Ussing chamber. As shown in FIG. 4, biochanin A further stimulated chloride secretion.

Example 2

Activation of Mutant CFTR by Representative Flavones and Isoflavones

This Example illustrates the use of the representative compounds apigenin, quercetin and genistein to activate ΔF508-CFTR and G551D-CFTR in different cell types.

Figure 5:
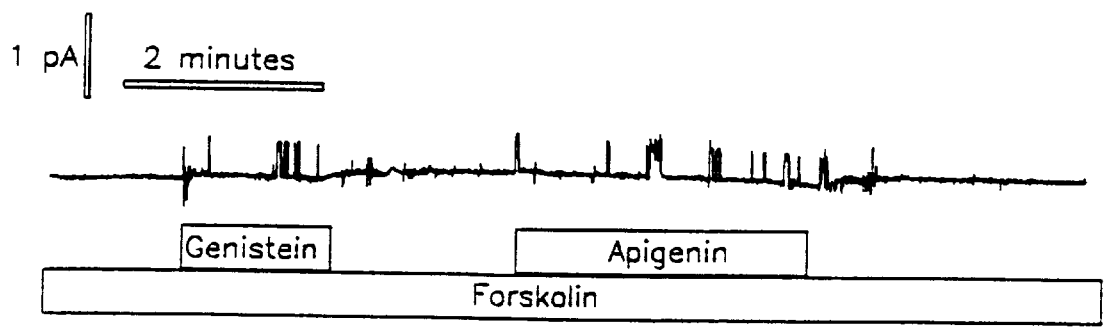
FIG. 5 is a cell-attached single channel patch clamp recording from a 3T3 cell expressing ΔF508-CFTR. The cell was treated with 10 μM forskolin as shown. Genistein (50 μM) and apigenin (50 μM), were added where indicated by boxes. The holding potential was 75 mV, and channel openings were upward.

A cell-attached single channel patch clamp recording was obtained from a 3T3 cell expressing ΔF508-CFTR as described by Hamill et al., *Pflugers Arch.* 391:85–100, 1981 and Fischer and Machen, *J. Gen. Physiol.* 104:541–566, 1994. As shown in FIG. 5, stimulation of the cell with 10 μM forskolin did not activate ΔF508-CFTR channel, but addition of genistein (50 μM) or apigenin (50 μM, where indicated by boxes) induced ΔF508-CFTR channel openings, and removal of these compounds inactivated the channels. The holding potential was 75 mV, and channel openings were upward.

Figure 6:
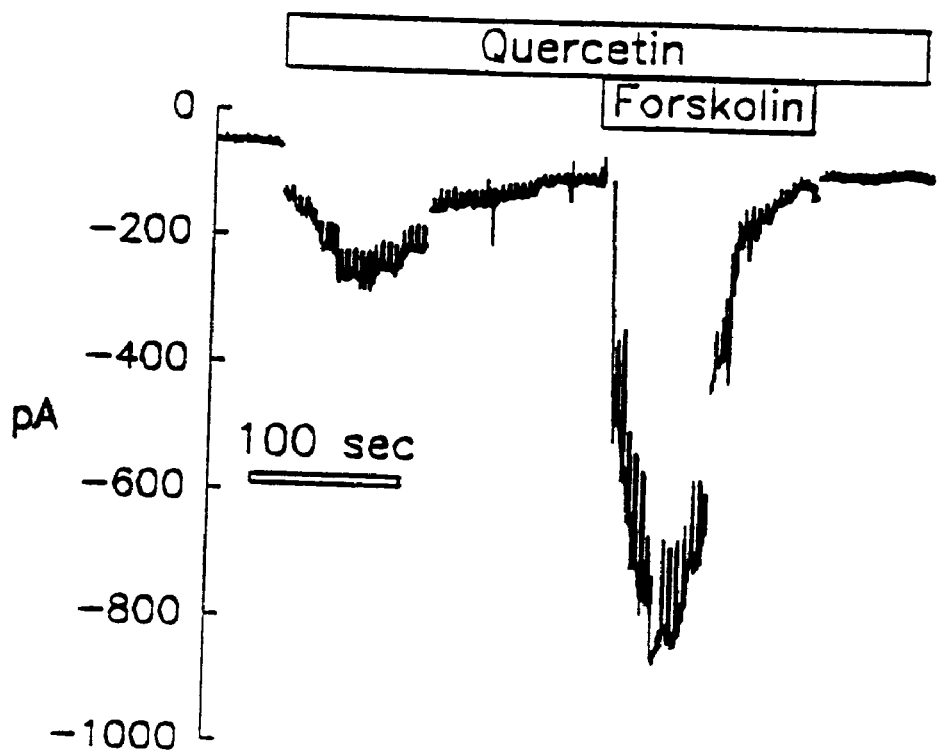
FIG. 6 is a whole cell patch clamp recording on an airway epithelial cell homozygous for ΔF508-CFTR. Before the measurement, the cell was incubated for 2 days in 5 mM 4-phenylbutyrate. 30 μM quercetin was added where indicated by the box. Further stimulation by forskolin (10 μM) is also shown. The holding potential was −60 mV.

FIG. 6 presents a whole cell patch clamp recording on an airway epithelial cell homozygous for ΔF508-CFTR (cell type: JME cell, see Jeffersen et al., *Am. J. Physiol.* 259:L496–L505, 1990). Before the measurement, the cell was incubated for 2 days in 5 mM 4-phenylbutyrate to enhance ΔF508-CFTR expression in the plasma membrane (Rubenstein & Zeitlin, *Ped. Pulm. Suppl.* 12:234, 1995). Measurements were performed as described by Fischer et al., *J. Physiol. Lond.* 489:745–754, 1995. Addition of 30 μM quercetin activated chloride current in the whole cell mode, which was further stimulated by forskolin. The holding potential was −60 mV.

Figure 7:
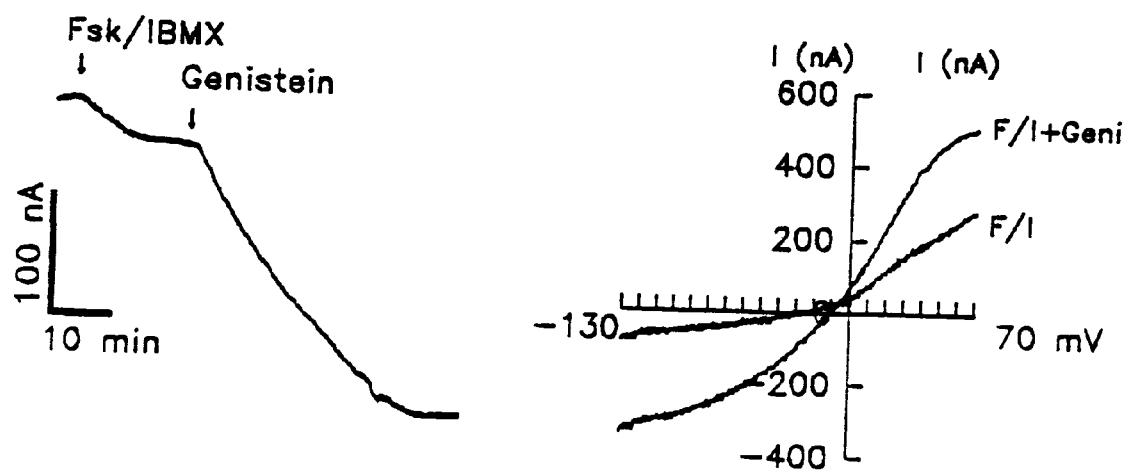
FIG. 7 is a recording illustrating the effect of genistein on G551D-CFTR expressed in a Xenopus oocyte. Current was measured with the two-electrode voltage clamp technique. G551D-CFTR was injected in oocyte. Current was first stimulated with forskolin (10 μM) and isobutylmethylxantine (IBMX; 2 mM). Genistein (50 μM) was added as indicated. The right panel shows current voltage relations recorded after treatment with forskolin and IBMX (F/I) and after treatment with genistein (F/I+Geni). A voltage ramp from −130 mV to +70 mV was applied and current was recorded during the two conditions.

The effect of genistein on chloride current in a Xenopus oocyte expressing G551D-CFTR was measured with the two-electrode voltage clamp technique (see Miledi et al., *Proc. R. Soc. Lond Biol.* 218:481–484, 1983). G55ID-CFTR (2 ng in 50 nL of water) was injected into the oocyte. Current was first stimulated with forskolin (10 μM) and isobutylmethylxantine (IBMX; 2 mM). Genistein (50 μM) was found to further activate chloride currents. As shown in FIG. 7, genistein increased conductance and shifted reversal potential to the right, which is indicative of a stimulated chloride current.

Example 3

Effect of Representative Flavones on Nasal Potential Difference

Figure 8:
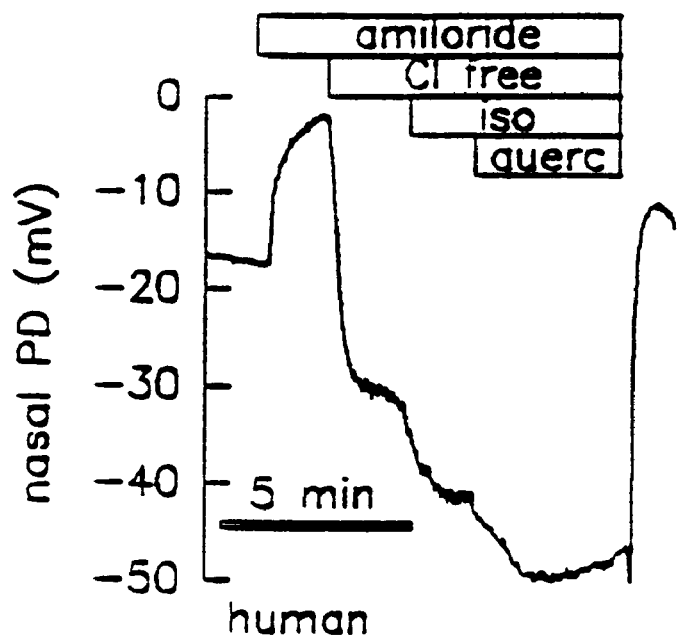
FIG. 8 is a recording illustrating the effect of quercetin on nasal potential difference (PD) measurement in a healthy human volunteer. Amiloride (50 μM) was added to block sodium transport as indicated. Conditions were rendered chloride free (Cl free) and chloride secretion was stimulated with isoproterenol (iso; 5 μM). Quercetin (querc; 10 μM) was added as indicated.
Figure 9:
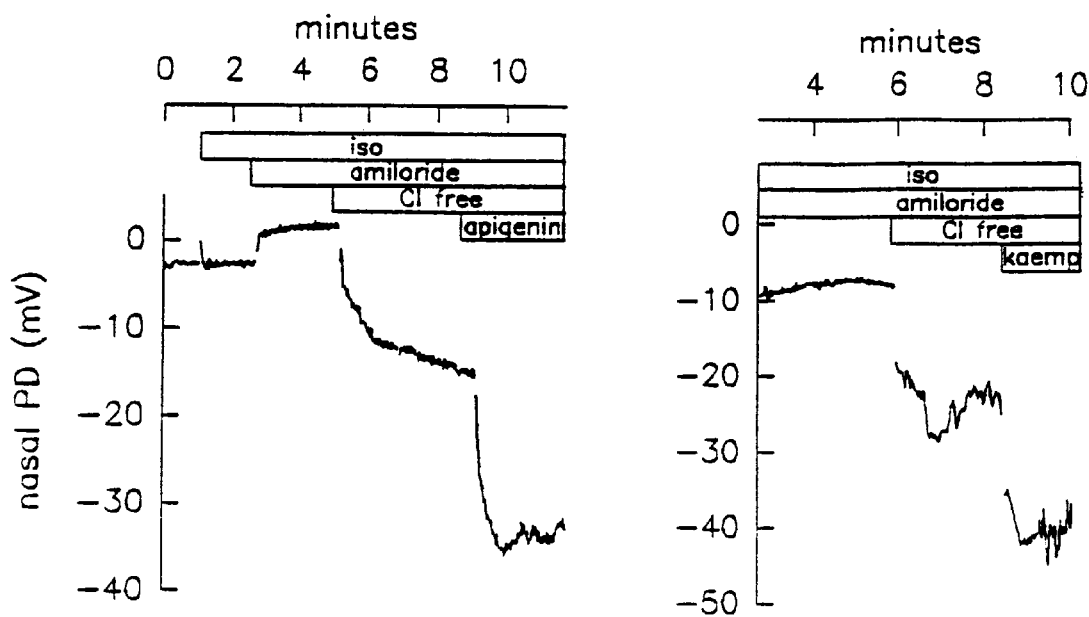
FIG. 9 is a recording illustrating the effect of apigenin and kaempferol on nasal PD in mice. Chloride secretion was stimulated with isoproterenol (iso; 5 μM), and amiloride (50 μM) was added to block sodium transport as indicated. Under chloride-free conditions (Cl free), apigenin (50 μM, left panel) and kaempferol (kaemp, 50 μM, right panel) were added as indicated.

This Example illustrates the in vivo use of quercetin, apigenin and kaempferol to activate the nasal potential difference in humans and mice. The effect of quercetin on nasal potential difference (PD) measurement in a healthy human volunteer was measured as described by Knowles et al., *Hum. Gene Therapy* 6:445–455, 1995. Under conditions where sodium transport was blocked with amiloride (50 μM) and chloride secretion was stimulated under chloride-free conditions with isoproterenol (5 μM), quercetin (10 μM) stimulated nasal PD further (FIG. 8).

The effect of apigenin and kaempferol on nasal PD in mice was evaluated using a method similar to that employed for measurements in humans, except that a plastic tube of approximately 0.1 mm diameter was used as an exploring nasal electrode. The plastic tube was perfused with test solutions at approximately 10 μL/min. After blocking sodium transport with amiloride (50 μM) and during stimulation of chloride secretion with isoproterenol (iso;5 μM) under chloride-free conditions, apigenin (50 μM, left panel) and kaempferol (kaemp, 50 μM, right panel) further stimulated nasal PD.

These results show that the representative flavonoids quercetin, apigenin, kaempferol and biochanin A stimulate chloride transport across epithelial tissues derived from the airways in vitro, and across nasal epithelium in vivo. The results also show that the CFTR mutants ΔF508 and G551D can be activated by the representative compounds genistein and apigenin.

From the foregoing, it will be appreciated that, although specific embodiments of the invention have been described herein for the purpose of illustration, various modifications may be made without deviating from the spirit and scope of the invention.

What is claimed is:

1. A method for enhancing chloride transport in epithelial cells, comprising contacting epithelial cells with a compound selected from the group consisting of flavones and isoflavones, wherein the compound is capable of stimulating chloride transport, and wherein the compound is not genistein.

2. A method according to claim 1, wherein the compound is quercetin, apigenin, kaempferol or biochanin A.

3. A method according to claim 1, wherein the epithelial cells are airway epithelial cells.

4. A method according to claim 3, wherein the airway epithelial cells are present in a mammal.

5. A method according to claim 4, wherein the compound is administered orally.

6. A method according to claim 4, wherein the compound is administered by inhalation.

7. A method according to claim 1, wherein the epithelial cells are intestinal cells.

8. A method according to claim 7, wherein the intestinal epithelial cells are present in a mammal.

9. A method according to claim 7, wherein the compound is administered orally.

10. A method according to claim 1, wherein the compound is present within a pharmaceutical composition.

11. A method according to claim 1, wherein the epithelial cells produce a CFTR protein having a deletion at position 508.

12. A method for treating cystic fibrosis in a mammal, comprising administering to a mammal one or more compounds selected from the group consisting of flavones and isoflavones, wherein the compound is capable of stimulating chloride secretion, and wherein the compound is not genistein.

13. A method according to claim 12, wherein the compound is quercetin, apigenin, kaempferol or biochanin A.

14. A method according to claim 12, wherein the compound is administered orally.

15. A method according to claim 12, wherein the compound is administered by inhalation.

16. A method according to claim 12, wherein the compound is present within a pharmaceutical composition.

17. A method for increasing chloride ion conductance in airway epithelial cells of a patient afflicted with cystic fibrosis, wherein the patient's CFTR protein has a deletion at position 508, the method comprising administering to a mammal one or more compounds selected from the group consisting of flavones and isoflavones, wherein the compound is capable of stimulating chloride secretion.

18. A pharmaceutical composition for treatment of cystic fibrosis, comprising one or more flavones or isoflavones capable of stimulating chloride secretion in combination with a pharmaceutically acceptable carrier, where the composition does not comprise genistein as an active ingredient, and wherein the composition further comprises 4-phenylbutyrate.

19. A pharmaceutical composition for treatment of cystic fibrosis, comprising quercetin in combination with a pharmaceutically acceptable carriers and wherein the composition further comprises 4-phenylbutyrate.

20. A pharmaceutical composition for treatment of cystic fibrosis, comprising apigenin in combination with a pharmaceutically acceptable carrier, and wherein the composition further comprises 4-phenylbutyrate.

21. A pharmaceutical composition for treatment of cystic fibrosis, comprising kaempferol in combination with a pharmaceutically acceptable carriers and wherein the composition further comprises 4-phenylbutyrate.

22. A pharmaceutical composition for treatment of cystic fibrosis, comprising biochanin A in combination with a pharmaceutically acceptable carrier, and wherein the composition further comprises 4-phenylbutyrate.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 6129 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 133..4572

(xi) SEQUENCE DESCRIPTION: SEQ ID NO:1:

```
AATTGGAAGC AAATGACATC ACAGCAGGTC AGAGAAAAAG GGTTGAGCGG CAGGCACCCA      60

GAGTAGTAGG TCTTTGGCAT TAGGAGCTTG AGCCCAGACG GCCCTAGCAG GGACCCCAGC     120
```

```
GCCCGAGAGA CC ATG CAG AGG TCG CCT CTG GAA AAG GCC AGC GTT GTC        168
              Met Gln Arg Ser Pro Leu Glu Lys Ala Ser Val Val
                1               5                  10

TCC AAA CTT TTT TTC AGC TGG ACC AGA CCA ATT TTG AGG AAA GGA TAC      216
Ser Lys Leu Phe Phe Ser Trp Thr Arg Pro Ile Leu Arg Lys Gly Tyr
        15                  20                  25

AGA CAG CGC CTG GAA TTG TCA GAC ATA TAC CAA ATC CCT TCT GTT GAT      264
Arg Gln Arg Leu Glu Leu Ser Asp Ile Tyr Gln Ile Pro Ser Val Asp
    30                  35                  40

TCT GCT GAC AAT CTA TCT GAA AAA TTG GAA AGA GAA TGG GAT AGA GAG      312
Ser Ala Asp Asn Leu Ser Glu Lys Leu Glu Arg Glu Trp Asp Arg Glu
45                  50                  55                  60

CTG GCT TCA AAG AAA AAT CCT AAA CTC ATT AAT GCC CTT CGG CGA TGT      360
Leu Ala Ser Lys Lys Asn Pro Lys Leu Ile Asn Ala Leu Arg Arg Cys
                65                  70                  75

TTT TTC TGG AGA TTT ATG TTC TAT GGA ATC TTT TTA TAT TTA GGG GAA      408
Phe Phe Trp Arg Phe Met Phe Tyr Gly Ile Phe Leu Tyr Leu Gly Glu
            80                  85                  90

GTC ACC AAA GCA GTA CAG CCT CTC TTA CTG GGA AGA ATC ATA GCT TCC      456
Val Thr Lys Ala Val Gln Pro Leu Leu Leu Gly Arg Ile Ile Ala Ser
        95                  100                 105

TAT GAC CCG GAT AAC AAG GAG GAA CGC TCT ATC GCG ATT TAT CTA GGC      504
Tyr Asp Pro Asp Asn Lys Glu Glu Arg Ser Ile Ala Ile Tyr Leu Gly
    110                 115                 120

ATA GGC TTA TGC CTT CTC TTT ATT GTG AGG ACA CTG CTC CTA CAC CCA      552
Ile Gly Leu Cys Leu Leu Phe Ile Val Arg Thr Leu Leu Leu His Pro
125                 130                 135                 140

GCC ATT TTT GGC CTT CAT CAC ATT GGA ATG CAG ATG AGA ATA GCT ATG      600
Ala Ile Phe Gly Leu His His Ile Gly Met Gln Met Arg Ile Ala Met
                145                 150                 155

TTT AGT TTG ATT TAT AAG AAG ACT TTA AAG CTG TCA AGC CGT GTT CTA      648
Phe Ser Leu Ile Tyr Lys Lys Thr Leu Lys Leu Ser Ser Arg Val Leu
            160                 165                 170

GAT AAA ATA AGT ATT GGA CAA CTT GTT AGT CTC CTT TCC AAC AAC CTG      696
Asp Lys Ile Ser Ile Gly Gln Leu Val Ser Leu Leu Ser Asn Asn Leu
        175                 180                 185

AAC AAA TTT GAT GAA GGA CTT GCA TTG GCA CAT TTC GTG TGG ATC GCT      744
Asn Lys Phe Asp Glu Gly Leu Ala Leu Ala His Phe Val Trp Ile Ala
    190                 195                 200

CCT TTG CAA GTG GCA CTC CTC ATG GGG CTA ATC TGG GAG TTG TTA CAG      792
Pro Leu Gln Val Ala Leu Leu Met Gly Leu Ile Trp Glu Leu Leu Gln
205                 210                 215                 220

GCG TCT GCC TTC TGT GGA CTT GGT TTC CTG ATA GTC CTT GCC CTT TTT      840
Ala Ser Ala Phe Cys Gly Leu Gly Phe Leu Ile Val Leu Ala Leu Phe
                225                 230                 235

CAG GCT GGG CTA GGG AGA ATG ATG ATG AAG TAC AGA GAT CAG AGA GCT      888
Gln Ala Gly Leu Gly Arg Met Met Met Lys Tyr Arg Asp Gln Arg Ala
            240                 245                 250

GGG AAG ATC AGT GAA AGA CTT GTG ATT ACC TCA GAA ATG ATT GAA AAT      936
Gly Lys Ile Ser Glu Arg Leu Val Ile Thr Ser Glu Met Ile Glu Asn
        255                 260                 265

ATC CAA TCT GTT AAG GCA TAC TGC TGG GAA GAA GCA ATG GAA AAA ATG      984
Ile Gln Ser Val Lys Ala Tyr Cys Trp Glu Glu Ala Met Glu Lys Met
    270                 275                 280

ATT GAA AAC TTA AGA CAA ACA GAA CTG AAA CTG ACT CGG AAG GCA GCC     1032
Ile Glu Asn Leu Arg Gln Thr Glu Leu Lys Leu Thr Arg Lys Ala Ala
285                 290                 295                 300

TAT GTG AGA TAC TTC AAT AGC TCA GCC TTC TTC TTC TCA GGG TTC TTT     1080
Tyr Val Arg Tyr Phe Asn Ser Ser Ala Phe Phe Phe Ser Gly Phe Phe
                305                 310                 315
```

-continued

| | | |
|---|---|---|
| GTG GTG TTT TTA TCT GTG CTT CCC TAT GCA CTA ATC AAA GGA ATC ATC<br>Val Val Phe Leu Ser Val Leu Pro Tyr Ala Leu Ile Lys Gly Ile Ile<br>          320                    325                330 | 1128 |
| CTC CGG AAA ATA TTC ACC ACC ATC TCA TTC TGC ATT GTT CTG CGC ATG<br>Leu Arg Lys Ile Phe Thr Thr Ile Ser Phe Cys Ile Val Leu Arg Met<br>        335                    340                  345 | 1176 |
| GCG GTC ACT CGG CAA TTT CCC TGG GCT GTA CAA ACA TGG TAT GAC TCT<br>Ala Val Thr Arg Gln Phe Pro Trp Ala Val Gln Thr Trp Tyr Asp Ser<br>          350                    355                360 | 1224 |
| CTT GGA GCA ATA AAC AAA ATA CAG GAT TTC TTA CAA AAG CAA GAA TAT<br>Leu Gly Ala Ile Asn Lys Ile Gln Asp Phe Leu Gln Lys Gln Glu Tyr<br>365                    370                  375                380 | 1272 |
| AAG ACA TTG GAA TAT AAC TTA ACG ACT ACA GAA GTA GTG ATG GAG AAT<br>Lys Thr Leu Glu Tyr Asn Leu Thr Thr Thr Glu Val Val Met Glu Asn<br>                    385                  390                395 | 1320 |
| GTA ACA GCC TTC TGG GAG GAG GGA TTT GGG GAA TTA TTT GAG AAA GCA<br>Val Thr Ala Phe Trp Glu Glu Gly Phe Gly Glu Leu Phe Glu Lys Ala<br>                400                  405                410 | 1368 |
| AAA CAA AAC AAT AAC AAT AGA AAA ACT TCT AAT GGT GAT GAC AGC CTC<br>Lys Gln Asn Asn Asn Asn Arg Lys Thr Ser Asn Gly Asp Asp Ser Leu<br>                415                  420                425 | 1416 |
| TTC TTC AGT AAT TTC TCA CTT CTT GGT ACT CCT GTC CTG AAA GAT ATT<br>Phe Phe Ser Asn Phe Ser Leu Leu Gly Thr Pro Val Leu Lys Asp Ile<br>        430                    435                  440 | 1464 |
| AAT TTC AAG ATA GAA AGA GGA CAG TTG TTG GCG GTT GCT GGA TCC ACT<br>Asn Phe Lys Ile Glu Arg Gly Gln Leu Leu Ala Val Ala Gly Ser Thr<br>445                    450                  455                460 | 1512 |
| GGA GCA GGC AAG ACT TCA CTT CTA ATG ATG ATT ATG GGA GAA CTG GAG<br>Gly Ala Gly Lys Thr Ser Leu Leu Met Met Ile Met Gly Glu Leu Glu<br>                    465                  470                475 | 1560 |
| CCT TCA GAG GGT AAA ATT AAG CAC AGT GGA AGA ATT TCA TTC TGT TCT<br>Pro Ser Glu Gly Lys Ile Lys His Ser Gly Arg Ile Ser Phe Cys Ser<br>                480                  485                490 | 1608 |
| CAG TTT TCC TGG ATT ATG CCT GGC ACC ATT AAA GAA AAT ATC ATC TTT<br>Gln Phe Ser Trp Ile Met Pro Gly Thr Ile Lys Glu Asn Ile Ile Phe<br>        495                    500                  505 | 1656 |
| GGT GTT TCC TAT GAT GAA TAT AGA TAC AGA AGC GTC ATC AAA GCA TGC<br>Gly Val Ser Tyr Asp Glu Tyr Arg Tyr Arg Ser Val Ile Lys Ala Cys<br>          510                    515                520 | 1704 |
| CAA CTA GAA GAG GAC ATC TCC AAG TTT GCA GAG AAA GAC AAT ATA GTT<br>Gln Leu Glu Glu Asp Ile Ser Lys Phe Ala Glu Lys Asp Asn Ile Val<br>525                    530                  535                540 | 1752 |
| CTT GGA GAA GGT GGA ATC ACA CTG AGT GGA GGT CAA CGA GCA AGA ATT<br>Leu Gly Glu Gly Gly Ile Thr Leu Ser Gly Gly Gln Arg Ala Arg Ile<br>                    545                  550                555 | 1800 |
| TCT TTA GCA AGA GCA GTA TAC AAA GAT GCT GAT TTG TAT TTA TTA GAC<br>Ser Leu Ala Arg Ala Val Tyr Lys Asp Ala Asp Leu Tyr Leu Leu Asp<br>          560                    565                570 | 1848 |
| TCT CCT TTT GGA TAC CTA GAT GTT TTA ACA GAA AAA GAA ATA TTT GAA<br>Ser Pro Phe Gly Tyr Leu Asp Val Leu Thr Glu Lys Glu Ile Phe Glu<br>        575                    580                  585 | 1896 |
| AGC TGT GTC TGT AAA CTG ATG GCT AAC AAA ACT AGG ATT TTG GTC ACT<br>Ser Cys Val Cys Lys Leu Met Ala Asn Lys Thr Arg Ile Leu Val Thr<br>        590                    595                  600 | 1944 |
| TCT AAA ATG GAA CAT TTA AAG AAA GCT GAC AAA ATA TTA ATT TTG AAT<br>Ser Lys Met Glu His Leu Lys Lys Ala Asp Lys Ile Leu Ile Leu Asn<br>605                    610                  615                620 | 1992 |
| GAA GGT AGC AGC TAT TTT TAT GGG ACA TTT TCA GAA CTC CAA AAT CTA<br>Glu Gly Ser Ser Tyr Phe Tyr Gly Thr Phe Ser Glu Leu Gln Asn Leu<br>                    625                  630                635 | 2040 |

-continued

```
CAG CCA GAC TTT AGC TCA AAA CTC ATG GGA TGT GAT TCT TTC GAC CAA        2088
Gln Pro Asp Phe Ser Ser Lys Leu Met Gly Cys Asp Ser Phe Asp Gln
            640                 645                 650

TTT AGT GCA GAA AGA AGA AAT TCA ATC CTA ACT GAG ACC TTA CAC CGT        2136
Phe Ser Ala Glu Arg Arg Asn Ser Ile Leu Thr Glu Thr Leu His Arg
            655                 660                 665

TTC TCA TTA GAA GGA GAT GCT CCT GTC TCC TGG ACA GAA ACA AAA AAA        2184
Phe Ser Leu Glu Gly Asp Ala Pro Val Ser Trp Thr Glu Thr Lys Lys
            670                 675                 680

CAA TCT TTT AAA CAG ACT GGA GAG TTT GGG GAA AAA AGG AAG AAT TCT        2232
Gln Ser Phe Lys Gln Thr Gly Glu Phe Gly Glu Lys Arg Lys Asn Ser
685                 690                 695                 700

ATT CTC AAT CCA ATC AAC TCT ATA CGA AAA TTT TCC ATT GTG CAA AAG        2280
Ile Leu Asn Pro Ile Asn Ser Ile Arg Lys Phe Ser Ile Val Gln Lys
                705                 710                 715

ACT CCC TTA CAA ATG AAT GGC ATC GAA GAG GAT TCT GAT GAG CCT TTA        2328
Thr Pro Leu Gln Met Asn Gly Ile Glu Glu Asp Ser Asp Glu Pro Leu
                720                 725                 730

GAG AGA AGG CTG TCC TTA GTA CCA GAT TCT GAG CAG GGA GAG GCG ATA        2376
Glu Arg Arg Leu Ser Leu Val Pro Asp Ser Glu Gln Gly Glu Ala Ile
                735                 740                 745

CTG CCT CGC ATC AGC GTG ATC AGC ACT GGC CCC ACG CTT CAG GCA CGA        2424
Leu Pro Arg Ile Ser Val Ile Ser Thr Gly Pro Thr Leu Gln Ala Arg
                750                 755                 760

AGG AGG CAG TCT GTC CTG AAC CTG ATG ACA CAC TCA GTT AAC CAA GGT        2472
Arg Arg Gln Ser Val Leu Asn Leu Met Thr His Ser Val Asn Gln Gly
765                 770                 775                 780

CAG AAC ATT CAC CGA AAG ACA ACA GCA TCC ACA CGA AAA GTG TCA CTG        2520
Gln Asn Ile His Arg Lys Thr Thr Ala Ser Thr Arg Lys Val Ser Leu
                785                 790                 795

GCC CCT CAG GCA AAC TTG ACT GAA CTG GAT ATA TAT TCA AGA AGG TTA        2568
Ala Pro Gln Ala Asn Leu Thr Glu Leu Asp Ile Tyr Ser Arg Arg Leu
                800                 805                 810

TCT CAA GAA ACT GGC TTG GAA ATA AGT GAA GAA ATT AAC GAA GAA GAC        2616
Ser Gln Glu Thr Gly Leu Glu Ile Ser Glu Glu Ile Asn Glu Glu Asp
                815                 820                 825

TTA AAG GAG TGC CTT TTT GAT GAT ATG GAG AGC ATA CCA GCA GTG ACT        2664
Leu Lys Glu Cys Leu Phe Asp Asp Met Glu Ser Ile Pro Ala Val Thr
830                 835                 840

ACA TGG AAC ACA TAC CTT CGA TAT ATT ACT GTC CAC AAG AGC TTA ATT        2712
Thr Trp Asn Thr Tyr Leu Arg Tyr Ile Thr Val His Lys Ser Leu Ile
845                 850                 855                 860

TTT GTG CTA ATT TGG TGC TTA GTA ATT TTT CTG GCA GAG GTG GCT GCT        2760
Phe Val Leu Ile Trp Cys Leu Val Ile Phe Leu Ala Glu Val Ala Ala
                865                 870                 875

TCT TTG GTT GTG CTG TGG CTC CTT GGA AAC ACT CCT CTT CAA GAC AAA        2808
Ser Leu Val Val Leu Trp Leu Leu Gly Asn Thr Pro Leu Gln Asp Lys
                880                 885                 890

GGG AAT AGT ACT CAT AGT AGA AAT AAC AGC TAT GCA GTG ATT ATC ACC        2856
Gly Asn Ser Thr His Ser Arg Asn Asn Ser Tyr Ala Val Ile Ile Thr
                895                 900                 905

AGC ACC AGT TCG TAT TAT GTG TTT TAC ATT TAC GTG GGA GTA GCC GAC        2904
Ser Thr Ser Ser Tyr Tyr Val Phe Tyr Ile Tyr Val Gly Val Ala Asp
                910                 915                 920

ACT TTG CTT GCT ATG GGA TTC TTC AGA GGT CTA CCA CTG GTG CAT ACT        2952
Thr Leu Leu Ala Met Gly Phe Phe Arg Gly Leu Pro Leu Val His Thr
925                 930                 935                 940

CTA ATC ACA GTG TCG AAA ATT TTA CAC CAC AAA ATG TTA CAT TCT GTT        3000
Leu Ile Thr Val Ser Lys Ile Leu His His Lys Met Leu His Ser Val
                945                 950                 955
```

-continued

```
CTT CAA GCA CCT ATG TCA ACC CTC AAC ACG TTG AAA GCA GGT GGG ATT    3048
Leu Gln Ala Pro Met Ser Thr Leu Asn Thr Leu Lys Ala Gly Gly Ile
            960                 965                 970

CTT AAT AGA TTC TCC AAA GAT ATA GCA ATT TTG GAT GAC CTT CTG CCT    3096
Leu Asn Arg Phe Ser Lys Asp Ile Ala Ile Leu Asp Asp Leu Leu Pro
            975                 980                 985

CTT ACC ATA TTT GAC TTC ATC CAG TTG TTA TTA ATT GTG ATT GGA GCT    3144
Leu Thr Ile Phe Asp Phe Ile Gln Leu Leu Leu Ile Val Ile Gly Ala
        990                 995                 1000

ATA GCA GTT GTC GCA GTT TTA CAA CCC TAC ATC TTT GTT GCA ACA GTG    3192
Ile Ala Val Val Ala Val Leu Gln Pro Tyr Ile Phe Val Ala Thr Val
1005                1010                1015                1020

CCA GTG ATA GTG GCT TTT ATT ATG TTG AGA GCA TAT TTC CTC CAA ACC    3240
Pro Val Ile Val Ala Phe Ile Met Leu Arg Ala Tyr Phe Leu Gln Thr
                1025                1030                1035

TCA CAG CAA CTC AAA CAA CTG GAA TCT GAA GGC AGG AGT CCA ATT TTC    3288
Ser Gln Gln Leu Lys Gln Leu Glu Ser Glu Gly Arg Ser Pro Ile Phe
                1040                1045                1050

ACT CAT CTT GTT ACA AGC TTA AAA GGA CTA TGG ACA CTT CGT GCC TTC    3336
Thr His Leu Val Thr Ser Leu Lys Gly Leu Trp Thr Leu Arg Ala Phe
                1055                1060                1065

GGA CGG CAG CCT TAC TTT GAA ACT CTG TTC CAC AAA GCT CTG AAT TTA    3384
Gly Arg Gln Pro Tyr Phe Glu Thr Leu Phe His Lys Ala Leu Asn Leu
            1070                1075                1080

CAT ACT GCC AAC TGG TTC TTG TAC CTG TCA ACA CTG CGC TGG TTC CAA    3432
His Thr Ala Asn Trp Phe Leu Tyr Leu Ser Thr Leu Arg Trp Phe Gln
1085                1090                1095                1100

ATG AGA ATA GAA ATG ATT TTT GTC ATC TTC TTC ATT GCT GTT ACC TTC    3480
Met Arg Ile Glu Met Ile Phe Val Ile Phe Phe Ile Ala Val Thr Phe
            1105                1110                1115

ATT TCC ATT TTA ACA ACA GGA GAA GGA GAA GGA AGA GTT GGT ATT ATC    3528
Ile Ser Ile Leu Thr Thr Gly Glu Gly Glu Gly Arg Val Gly Ile Ile
            1120                1125                1130

CTG ACT TTA GCC ATG AAT ATC ATG AGT ACA TTG CAG TGG GCT GTA AAC    3576
Leu Thr Leu Ala Met Asn Ile Met Ser Thr Leu Gln Trp Ala Val Asn
            1135                1140                1145

TCC AGC ATA GAT GTG GAT AGC TTG ATG CGA TCT GTG AGC CGA GTC TTT    3624
Ser Ser Ile Asp Val Asp Ser Leu Met Arg Ser Val Ser Arg Val Phe
        1150                1155                1160

AAG TTC ATT GAC ATG CCA ACA GAA GGT AAA CCT ACC AAG TCA ACC AAA    3672
Lys Phe Ile Asp Met Pro Thr Glu Gly Lys Pro Thr Lys Ser Thr Lys
1165                1170                1175                1180

CCA TAC AAG AAT GGC CAA CTC TCG AAA GTT ATG ATT ATT GAG AAT TCA    3720
Pro Tyr Lys Asn Gly Gln Leu Ser Lys Val Met Ile Ile Glu Asn Ser
                1185                1190                1195

CAC GTG AAG AAA GAT GAC ATC TGG CCC TCA GGG GGC CAA ATG ACT GTC    3768
His Val Lys Lys Asp Asp Ile Trp Pro Ser Gly Gly Gln Met Thr Val
                1200                1205                1210

AAA GAT CTC ACA GCA AAA TAC ACA GAA GGT GGA AAT GCC ATA TTA GAG    3816
Lys Asp Leu Thr Ala Lys Tyr Thr Glu Gly Gly Asn Ala Ile Leu Glu
            1215                1220                1225

AAC ATT TCC TTC TCA ATA AGT CCT GGC CAG AGG GTG GGC CTC TTG GGA    3864
Asn Ile Ser Phe Ser Ile Ser Pro Gly Gln Arg Val Gly Leu Leu Gly
            1230                1235                1240

AGA ACT GGA TCA GGG AAG AGT ACT TTG TTA TCA GCT TTT TTG AGA CTA    3912
Arg Thr Gly Ser Gly Lys Ser Thr Leu Leu Ser Ala Phe Leu Arg Leu
1245                1250                1255                1260

CTG AAC ACT GAA GGA GAA ATC CAG ATC GAT GGT GTG TCT TGG GAT TCA    3960
Leu Asn Thr Glu Gly Glu Ile Gln Ile Asp Gly Val Ser Trp Asp Ser
                1265                1270                1275
```

-continued

| | |
|---|---|
| ATA ACT TTG CAA CAG TGG AGG AAA GCC TTT GGA GTG ATA CCA CAG AAA<br>Ile Thr Leu Gln Gln Trp Arg Lys Ala Phe Gly Val Ile Pro Gln Lys<br>                1280                      1285                    1290 | 4008 |
| GTA TTT ATT TTT TCT GGA ACA TTT AGA AAA AAC TTG GAT CCC TAT GAA<br>Val Phe Ile Phe Ser Gly Thr Phe Arg Lys Asn Leu Asp Pro Tyr Glu<br>                1295                      1300                    1305 | 4056 |
| CAG TGG AGT GAT CAA GAA ATA TGG AAA GTT GCA GAT GAG GTT GGG CTC<br>Gln Trp Ser Asp Gln Glu Ile Trp Lys Val Ala Asp Glu Val Gly Leu<br>1310                      1315                    1320 | 4104 |
| AGA TCT GTG ATA GAA CAG TTT CCT GGG AAG CTT GAC TTT GTC CTT GTG<br>Arg Ser Val Ile Glu Gln Phe Pro Gly Lys Leu Asp Phe Val Leu Val<br>1325                      1330                    1335                    1340 | 4152 |
| GAT GGG GGC TGT GTC CTA AGC CAT GGC CAC AAG CAG TTG ATG TGC TTG<br>Asp Gly Gly Cys Val Leu Ser His Gly His Lys Gln Leu Met Cys Leu<br>                1345                      1350                    1355 | 4200 |
| GCT AGA TCT GTT CTC AGT AAG GCG AAG ATC TTG CTG CTT GAT GAA CCC<br>Ala Arg Ser Val Leu Ser Lys Ala Lys Ile Leu Leu Leu Asp Glu Pro<br>                1360                      1365                    1370 | 4248 |
| AGT GCT CAT TTG GAT CCA GTA ACA TAC CAA ATA ATT AGA AGA ACT CTA<br>Ser Ala His Leu Asp Pro Val Thr Tyr Gln Ile Ile Arg Arg Thr Leu<br>                1375                      1380                    1385 | 4296 |
| AAA CAA GCA TTT GCT GAT TGC ACA GTA ATT CTC TGT GAA CAC AGG ATA<br>Lys Gln Ala Phe Ala Asp Cys Thr Val Ile Leu Cys Glu His Arg Ile<br>                1390                      1395                    1400 | 4344 |
| GAA GCA ATG CTG GAA TGC CAA CAA TTT TTG GTC ATA GAA GAG AAC AAA<br>Glu Ala Met Leu Glu Cys Gln Gln Phe Leu Val Ile Glu Glu Asn Lys<br>1405                      1410                    1415                    1420 | 4392 |
| GTG CGG CAG TAC GAT TCC ATC CAG AAA CTG CTG AAC GAG AGG AGC CTC<br>Val Arg Gln Tyr Asp Ser Ile Gln Lys Leu Leu Asn Glu Arg Ser Leu<br>                1425                      1430                    1435 | 4440 |
| TTC CGG CAA GCC ATC AGC CCC TCC GAC AGG GTG AAG CTC TTT CCC CAC<br>Phe Arg Gln Ala Ile Ser Pro Ser Asp Arg Val Lys Leu Phe Pro His<br>                1440                      1445                    1450 | 4488 |
| CGG AAC TCA AGC AAG TGC AAG TCT AAG CCC CAG ATT GCT GCT CTG AAA<br>Arg Asn Ser Ser Lys Cys Lys Ser Lys Pro Gln Ile Ala Ala Leu Lys<br>                1455                      1460                    1465 | 4536 |
| GAG GAG ACA GAA GAA GAG GTG CAA GAT ACA AGG CTT TAGAGAGCAG<br>Glu Glu Thr Glu Glu Glu Val Gln Asp Thr Arg Leu<br>1470                    1475                    1480 | 4582 |
| CATAAATGTT GACATGGGAC ATTTGCTCAT GGAATTGGAG CTCGTGGGAC AGTCACCTCA | 4642 |
| TGGAATTGGA GCTCGTGGAA CAGTTACCTC TGCCTCAGAA AACAAGGATG AATTAAGTTT | 4702 |
| TTTTTTAAAA AAGAAACATT TGGTAAGGGG AATTGAGGAC ACTGATATGG GTCTTGATAA | 4762 |
| ATGGCTTCCT GGCAATAGTC AAATTGTGTG AAAGGTACTT CAAATCCTTG AAGATTTACC | 4822 |
| ACTTGTGTTT TGCAAGCCAG ATTTTCCTGA AAACCCTTGC CATGTGCTAG TAATTGGAAA | 4882 |
| GGCAGCTCTA AATGTCAATC AGCCTAGTTG ATCAGCTTAT TGTCTAGTGA AACTCGTTAA | 4942 |
| TTTGTAGTGT TGGAGAAGAA CTGAAATCAT ACTTCTTAGG GTTATGATTA AGTAATGATA | 5002 |
| ACTGGAAACT TCAGCGGTTT ATATAAGCTT GTATTCCTTT TTCTCTCCTC TCCCCATGAT | 5062 |
| GTTTAGAAAC ACAACTATAT TGTTTGCTAA GCATTCCAAC TATCTCATTT CCAAGCAAGT | 5122 |
| ATTAGAATAC CACAGGAACC ACAAGACTGC ACATCAAAAT ATGCCCCATT CAACATCTAG | 5182 |
| TGAGCAGTCA GGAAAGAGAA CTTCCAGATC CTGGAAATCA GGGTTAGTAT TGTCCAGGTC | 5242 |
| TACCAAAAAT CTCAATATTT CAGATAATCA CAATACATCC CTTACCTGGG AAAGGGCTGT | 5302 |
| TATAATCTTT CACAGGGGAC AGGATGGTTC CCTTGATGAA GAAGTTGATA TGCCTTTTCC | 5362 |
| CAACTCCAGA AAGTGACAAG CTCACAGACC TTTGAACTAG AGTTTAGCTG GAAAAGTATG | 5422 |

```
TTAGTGCAAA TTGTCACAGG ACAGCCCTTC TTTCCACAGA AGCTCCAGGT AGAGGGTGTG      5482

TAAGTAGATA GGCCATGGGC ACTGTGGGTA GACACACATG AAGTCCAAGC ATTTAGATGT      5542

ATAGGTTGAT GGTGGTATGT TTTCAGGCTA GATGTATGTA CTTCATGCTG TCTACACTAA      5602

GAGAGAATGA GAGACACACT GAAGAAGCAC CAATCATGAA TTAGTTTTAT ATGCTTCTGT      5662

TTTATAATTT TGTGAAGCAA AATTTTTTCT CTAGGAAATA TTTATTTTAA TAATGTTTCA      5722

AACATATATT ACAATGCTGT ATTTTAAAAG AATGATTATG AATTACATTT GTATAAAATA      5782

ATTTTTATAT TTGAAATATT GACTTTTTAT GGCACTAGTA TTTTTATGAA ATATTATGTT      5842

AAAACTGGGA CAGGGGAGAA CCTAGGGTGA TATTAACCAG GGGCCATGAA TCACCTTTTG      5902

GTCTGGAGGG AAGCCTTGGG GCTGATCGAG TTGTTGCCCA CAGCTGTATG ATTCCCAGCC      5962

AGACACAGCC TCTTAGATGC AGTTCTGAAG AAGATGGTAC CACCAGTCTG ACTGTTTCCA      6022

TCAAGGGTAC ACTGCCTTCT CAACTCCAAA CTGACTCTTA AGAAGACTGC ATTATATTTA      6082

TTACTGTAAG AAAATATCAC TTGTCAATAA AATCCATACA TTTGTGT                   6129

(2) INFORMATION FOR SEQ ID NO:2:

(i) SEQUENCE CHARACTERISTICS:
        (A) LENGTH: 1480 amino acids
        (B) TYPE: amino acid
        (D) TOPOLOGY: linear (ii) MOLECULE TYPE: protein (xi) SEQUENCE DESCRIPTION: SEQ ID NO:2:

Met Gln Arg Ser Pro Leu Glu Lys Ala Ser Val Val Ser Lys Leu Phe
  1               5                  10                  15

Phe Ser Trp Thr Arg Pro Ile Leu Arg Lys Gly Tyr Arg Gln Arg Leu
                 20                  25                  30

Glu Leu Ser Asp Ile Tyr Gln Ile Pro Ser Val Asp Ser Ala Asp Asn
             35                  40                  45

Leu Ser Glu Lys Leu Glu Arg Glu Trp Asp Arg Glu Leu Ala Ser Lys
         50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
```

-continued

```
              225                 230                 235                 240
Gly Arg Met Met Met Lys Tyr Arg Asp Gln Arg Ala Gly Lys Ile Ser
                    245                 250                 255
Glu Arg Leu Val Ile Thr Ser Glu Met Ile Glu Asn Ile Gln Ser Val
                260                 265                 270
Lys Ala Tyr Cys Trp Glu Ala Met Glu Lys Met Ile Glu Asn Leu
            275                 280                 285
Arg Gln Thr Glu Leu Lys Leu Thr Arg Lys Ala Ala Tyr Val Arg Tyr
        290                 295                 300
Phe Asn Ser Ser Ala Phe Phe Ser Gly Phe Val Val Phe Leu
305                 310                 315                 320
Ser Val Leu Pro Tyr Ala Leu Ile Lys Gly Ile Ile Leu Arg Lys Ile
                325                 330                 335
Phe Thr Thr Ile Ser Phe Cys Ile Val Leu Arg Met Ala Val Thr Arg
                340                 345                 350
Gln Phe Pro Trp Ala Val Gln Thr Trp Tyr Asp Ser Leu Gly Ala Ile
                355                 360                 365
Asn Lys Ile Gln Asp Phe Leu Gln Lys Gln Tyr Lys Thr Leu Glu
370                 375                 380
Tyr Asn Leu Thr Thr Thr Glu Val Val Met Glu Asn Val Thr Ala Phe
385                 390                 395                 400
Trp Glu Glu Gly Phe Gly Glu Leu Phe Glu Lys Ala Lys Gln Asn Asn
                405                 410                 415
Asn Asn Arg Lys Thr Ser Asn Gly Asp Asp Ser Leu Phe Phe Ser Asn
                420                 425                 430
Phe Ser Leu Leu Gly Thr Pro Val Leu Lys Asp Ile Asn Phe Lys Ile
            435                 440                 445
Glu Arg Gly Gln Leu Leu Ala Val Ala Gly Ser Thr Gly Ala Gly Lys
450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
                500                 505                 510
Asp Glu Tyr Arg Tyr Arg Ser Val Ile Lys Ala Cys Gln Leu Glu Glu
            515                 520                 525
Asp Ile Ser Lys Phe Ala Glu Lys Asp Asn Ile Val Leu Gly Glu Gly
            530                 535                 540
Gly Ile Thr Leu Ser Gly Gly Gln Arg Ala Arg Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
                580                 585                 590
Lys Leu Met Ala Asn Lys Thr Arg Ile Leu Val Thr Ser Lys Met Glu
                595                 600                 605
His Leu Lys Lys Ala Asp Lys Ile Leu Ile Leu Asn Glu Gly Ser Ser
            610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
```

-continued

```
Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
                740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Leu Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
            850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
                900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
            930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile Val
        1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
                1060                1065                1070

Tyr Phe Glu Thr Leu Phe His Lys Ala Leu Asn Leu His Thr Ala Asn
            1075                1080                1085
```

```
Trp Phe Leu Tyr Leu Ser Thr Leu Arg Trp Phe Gln Met Arg Ile Glu
    1090            1095            1100

Met Ile Phe Val Ile Phe Phe Ile Ala Val Thr Phe Ile Ser Ile Leu
1105            1110            1115            1120

Thr Thr Gly Glu Gly Glu Gly Arg Val Gly Ile Ile Leu Thr Leu Ala
        1125            1130            1135

Met Asn Ile Met Ser Thr Leu Gln Trp Ala Val Asn Ser Ser Ile Asp
    1140            1145            1150

Val Asp Ser Leu Met Arg Ser Val Ser Arg Val Phe Lys Phe Ile Asp
        1155            1160            1165

Met Pro Thr Glu Gly Lys Pro Thr Lys Ser Thr Lys Pro Tyr Lys Asn
    1170            1175            1180

Gly Gln Leu Ser Lys Val Met Ile Ile Glu Asn Ser His Val Lys Lys
1185            1190            1195            1200

Asp Asp Ile Trp Pro Ser Gly Gly Gln Met Thr Val Lys Asp Leu Thr
        1205            1210            1215

Ala Lys Tyr Thr Glu Gly Gly Asn Ala Ile Leu Glu Asn Ile Ser Phe
        1220            1225            1230

Ser Ile Ser Pro Gly Gln Arg Val Gly Leu Leu Gly Arg Thr Gly Ser
        1235            1240            1245

Gly Lys Ser Thr Leu Leu Ser Ala Phe Leu Arg Leu Leu Asn Thr Glu
    1250            1255            1260

Gly Glu Ile Gln Ile Asp Gly Val Ser Trp Asp Ser Ile Thr Leu Gln
1265            1270            1275            1280

Gln Trp Arg Lys Ala Phe Gly Val Ile Pro Gln Lys Val Phe Ile Phe
        1285            1290            1295

Ser Gly Thr Phe Arg Lys Asn Leu Asp Pro Tyr Glu Gln Trp Ser Asp
        1300            1305            1310

Gln Glu Ile Trp Lys Val Ala Asp Glu Val Gly Leu Arg Ser Val Ile
        1315            1320            1325

Glu Gln Phe Pro Gly Lys Leu Asp Phe Val Leu Val Asp Gly Gly Cys
        1330            1335            1340

Val Leu Ser His Gly His Lys Gln Leu Met Cys Leu Ala Arg Ser Val
1345            1350            1355            1360

Leu Ser Lys Ala Lys Ile Leu Leu Leu Asp Glu Pro Ser Ala His Leu
        1365            1370            1375

Asp Pro Val Thr Tyr Gln Ile Ile Arg Arg Thr Leu Lys Gln Ala Phe
        1380            1385            1390

Ala Asp Cys Thr Val Ile Leu Cys Glu His Arg Ile Glu Ala Met Leu
        1395            1400            1405

Glu Cys Gln Gln Phe Leu Val Ile Glu Glu Asn Lys Val Arg Gln Tyr
    1410            1415            1420

Asp Ser Ile Gln Lys Leu Leu Asn Glu Arg Ser Leu Phe Arg Gln Ala
1425            1430            1435            1440

Ile Ser Pro Ser Asp Arg Val Lys Leu Phe Pro His Arg Asn Ser Ser
        1445            1450            1455

Lys Cys Lys Ser Lys Pro Gln Ile Ala Ala Leu Lys Glu Glu Thr Glu
        1460            1465            1470

Glu Glu Val Gln Asp Thr Arg Leu
        1475            1480

(2) INFORMATION FOR SEQ ID NO:3:

(i) SEQUENCE CHARACTERISTICS:
```

(A) LENGTH: 6126 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 133..4569

(xi) SEQUENCE DESCRIPTION: SEQ ID NO:3:

```
AATTGGAAGC AAATGACATC ACAGCAGGTC AGAGAAAAAG GGTTGAGCGG CAGGCACCCA      60

GAGTAGTAGG TCTTTGGCAT TAGGAGCTTG AGCCCAGACG GCCCTAGCAG GGACCCCAGC     120

GCCCGAGAGA CC ATG CAG AGG TCG CCT CTG GAA AAG GCC AGC GTT GTC        168
              Met Gln Arg Ser Pro Leu Glu Lys Ala Ser Val Val
                1               5                  10

TCC AAA CTT TTT TTC AGC TGG ACC AGA CCA ATT TTG AGG AAA GGA TAC      216
Ser Lys Leu Phe Phe Ser Trp Thr Arg Pro Ile Leu Arg Lys Gly Tyr
         15                  20                  25

AGA CAG CGC CTG GAA TTG TCA GAC ATA TAC CAA ATC CCT TCT GTT GAT      264
Arg Gln Arg Leu Glu Leu Ser Asp Ile Tyr Gln Ile Pro Ser Val Asp
     30                  35                  40

TCT GCT GAC AAT CTA TCT GAA AAA TTG GAA AGA GAA TGG GAT AGA GAG      312
Ser Ala Asp Asn Leu Ser Glu Lys Leu Glu Arg Glu Trp Asp Arg Glu
 45                  50                  55                  60

CTG GCT TCA AAG AAA AAT CCT AAA CTC ATT AAT GCC CTT CGG CGA TGT      360
Leu Ala Ser Lys Lys Asn Pro Lys Leu Ile Asn Ala Leu Arg Arg Cys
                 65                  70                  75

TTT TTC TGG AGA TTT ATG TTC TAT GGA ATC TTT TTA TAT TTA GGG GAA      408
Phe Phe Trp Arg Phe Met Phe Tyr Gly Ile Phe Leu Tyr Leu Gly Glu
             80                  85                  90

GTC ACC AAA GCA GTA CAG CCT CTC TTA CTG GGA AGA ATC ATA GCT TCC      456
Val Thr Lys Ala Val Gln Pro Leu Leu Leu Gly Arg Ile Ile Ala Ser
         95                 100                 105

TAT GAC CCG GAT AAC AAG GAG GAA CGC TCT ATC GCG ATT TAT CTA GGC      504
Tyr Asp Pro Asp Asn Lys Glu Glu Arg Ser Ile Ala Ile Tyr Leu Gly
     110                 115                 120

ATA GGC TTA TGC CTT CTC TTT ATT GTG AGG ACA CTG CTC CTA CAC CCA      552
Ile Gly Leu Cys Leu Leu Phe Ile Val Arg Thr Leu Leu Leu His Pro
125                 130                 135                 140

GCC ATT TTT GGC CTT CAT CAC ATT GGA ATG CAG ATG AGA ATA GCT ATG      600
Ala Ile Phe Gly Leu His His Ile Gly Met Gln Met Arg Ile Ala Met
                145                 150                 155

TTT AGT TTG ATT TAT AAG AAG ACT TTA AAG CTG TCA AGC CGT GTT CTA      648
Phe Ser Leu Ile Tyr Lys Lys Thr Leu Lys Leu Ser Ser Arg Val Leu
            160                 165                 170

GAT AAA ATA AGT ATT GGA CAA CTT GTT AGT CTC CTT TCC AAC AAC CTG      696
Asp Lys Ile Ser Ile Gly Gln Leu Val Ser Leu Leu Ser Asn Asn Leu
        175                 180                 185

AAC AAA TTT GAT GAA GGA CTT GCA TTG GCA CAT TTC GTG TGG ATC GCT      744
Asn Lys Phe Asp Glu Gly Leu Ala Leu Ala His Phe Val Trp Ile Ala
    190                 195                 200

CCT TTG CAA GTG GCA CTC CTC ATG GGG CTA ATC TGG GAG TTG TTA CAG      792
Pro Leu Gln Val Ala Leu Leu Met Gly Leu Ile Trp Glu Leu Leu Gln
205                 210                 215                 220

GCG TCT GCC TTC TGT GGA CTT GGT TTC CTG ATA GTC CTT GCC CTT TTT      840
Ala Ser Ala Phe Cys Gly Leu Gly Phe Leu Ile Val Leu Ala Leu Phe
                225                 230                 235

CAG GCT GGG CTA GGG AGA ATG ATG ATG AAG TAC AGA GAT CAG AGA GCT      888
Gln Ala Gly Leu Gly Arg Met Met Met Lys Tyr Arg Asp Gln Arg Ala
            240                 245                 250

GGG AAG ATC AGT GAA AGA CTT GTG ATT ACC TCA GAA ATG ATT GAA AAT      936
```

-continued

```
                    Gly Lys Ile Ser Glu Arg Leu Val Ile Thr Ser Glu Met Ile Glu Asn
                                    255                 260                 265

ATC CAA TCT GTT AAG GCA TAC TGC TGG GAA GAA GCA ATG GAA AAA ATG              984
Ile Gln Ser Val Lys Ala Tyr Cys Trp Glu Glu Ala Met Glu Lys Met
        270                 275                 280

ATT GAA AAC TTA AGA CAA ACA GAA CTG AAA CTG ACT CGG AAG GCA GCC             1032
Ile Glu Asn Leu Arg Gln Thr Glu Leu Lys Leu Thr Arg Lys Ala Ala
285                 290                 295                 300

TAT GTG AGA TAC TTC AAT AGC TCA GCC TTC TTC TTC TCA GGG TTC TTT             1080
Tyr Val Arg Tyr Phe Asn Ser Ser Ala Phe Phe Phe Ser Gly Phe Phe
                    305                 310                 315

GTG GTG TTT TTA TCT GTG CTT CCC TAT GCA CTA ATC AAA GGA ATC ATC             1128
Val Val Phe Leu Ser Val Leu Pro Tyr Ala Leu Ile Lys Gly Ile Ile
            320                 325                 330

CTC CGG AAA ATA TTC ACC ACC ATC TCA TTC TGC ATT GTT CTG CGC ATG             1176
Leu Arg Lys Ile Phe Thr Thr Ile Ser Phe Cys Ile Val Leu Arg Met
        335                 340                 345

GCG GTC ACT CGG CAA TTT CCC TGG GCT GTA CAA ACA TGG TAT GAC TCT             1224
Ala Val Thr Arg Gln Phe Pro Trp Ala Val Gln Thr Trp Tyr Asp Ser
350                 355                 360

CTT GGA GCA ATA AAC AAA ATA CAG GAT TTC TTA CAA AAG CAA GAA TAT             1272
Leu Gly Ala Ile Asn Lys Ile Gln Asp Phe Leu Gln Lys Gln Glu Tyr
365                 370                 375                 380

AAG ACA TTG GAA TAT AAC TTA ACG ACT ACA GAA GTA GTG ATG GAG AAT             1320
Lys Thr Leu Glu Tyr Asn Leu Thr Thr Thr Glu Val Val Met Glu Asn
                    385                 390                 395

GTA ACA GCC TTC TGG GAG GAG GGA TTT GGG GAA TTA TTT GAG AAA GCA             1368
Val Thr Ala Phe Trp Glu Glu Gly Phe Gly Glu Leu Phe Glu Lys Ala
            400                 405                 410

AAA CAA AAC AAT AAC AAT AGA AAA ACT TCT AAT GGT GAT GAC AGC CTC             1416
Lys Gln Asn Asn Asn Asn Arg Lys Thr Ser Asn Gly Asp Asp Ser Leu
        415                 420                 425

TTC TTC AGT AAT TTC TCA CTT CTT GGT ACT CCT GTC CTG AAA GAT ATT             1464
Phe Phe Ser Asn Phe Ser Leu Leu Gly Thr Pro Val Leu Lys Asp Ile
430                 435                 440

AAT TTC AAG ATA GAA AGA GGA CAG TTG TTG GCG GTT GCT GGA TCC ACT             1512
Asn Phe Lys Ile Glu Arg Gly Gln Leu Leu Ala Val Ala Gly Ser Thr
445                 450                 455                 460

GGA GCA GGC AAG ACT TCA CTT CTA ATG ATG ATT ATG GGA GAA CTG GAG             1560
Gly Ala Gly Lys Thr Ser Leu Leu Met Met Ile Met Gly Glu Leu Glu
                    465                 470                 475

CCT TCA GAG GGT AAA ATT AAG CAC AGT GGA AGA ATT TCA TTC TGT TCT             1608
Pro Ser Glu Gly Lys Ile Lys His Ser Gly Arg Ile Ser Phe Cys Ser
            480                 485                 490

CAG TTT TCC TGG ATT ATG CCT GGC ACC ATT AAA GAA AAT ATC ATC GGT             1656
Gln Phe Ser Trp Ile Met Pro Gly Thr Ile Lys Glu Asn Ile Ile Gly
        495                 500                 505

GTT TCC TAT GAT GAA TAT AGA TAC AGA AGC GTC ATC AAA GCA TGC CAA             1704
Val Ser Tyr Asp Glu Tyr Arg Tyr Arg Ser Val Ile Lys Ala Cys Gln
510                 515                 520

CTA GAA GAG GAC ATC TCC AAG TTT GCA GAG AAA GAC AAT ATA GTT CTT             1752
Leu Glu Glu Asp Ile Ser Lys Phe Ala Glu Lys Asp Asn Ile Val Leu
525                 530                 535                 540

GGA GAA GGT GGA ATC ACA CTG AGT GGA GGT CAA CGA GCA AGA ATT TCT             1800
Gly Glu Gly Gly Ile Thr Leu Ser Gly Gly Gln Arg Ala Arg Ile Ser
                    545                 550                 555

TTA GCA AGA GCA GTA TAC AAA GAT GCT GAT TTG TAT TTA TTA GAC TCT             1848
Leu Ala Arg Ala Val Tyr Lys Asp Ala Asp Leu Tyr Leu Leu Asp Ser
            560                 565                 570

CCT TTT GGA TAC CTA GAT GTT TTA ACA GAA AAA GAA ATA TTT GAA AGC             1896
```

```
              Pro Phe Gly Tyr Leu Asp Val Leu Thr Glu Lys Glu Ile Phe Glu Ser
                      575                 580                 585

TGT GTC TGT AAA CTG ATG GCT AAC AAA ACT AGG ATT TTG GTC ACT TCT             1944
Cys Val Cys Lys Leu Met Ala Asn Lys Thr Arg Ile Leu Val Thr Ser
        590                 595                 600

AAA ATG GAA CAT TTA AAG AAA GCT GAC AAA ATA TTA ATT TTG AAT GAA             1992
Lys Met Glu His Leu Lys Lys Ala Asp Lys Ile Leu Ile Leu Asn Glu
605                 610                 615                 620

GGT AGC AGC TAT TTT TAT GGG ACA TTT TCA GAA CTC CAA AAT CTA CAG             2040
Gly Ser Ser Tyr Phe Tyr Gly Thr Phe Ser Glu Leu Gln Asn Leu Gln
                    625                 630                 635

CCA GAC TTT AGC TCA AAA CTC ATG GGA TGT GAT TCT TTC GAC CAA TTT             2088
Pro Asp Phe Ser Ser Lys Leu Met Gly Cys Asp Ser Phe Asp Gln Phe
            640                 645                 650

AGT GCA GAA AGA AGA AAT TCA ATC CTA ACT GAG ACC TTA CAC CGT TTC             2136
Ser Ala Glu Arg Arg Asn Ser Ile Leu Thr Glu Thr Leu His Arg Phe
                655                 660                 665

TCA TTA GAA GGA GAT GCT CCT GTC TCC TGG ACA GAA ACA AAA AAA CAA             2184
Ser Leu Glu Gly Asp Ala Pro Val Ser Trp Thr Glu Thr Lys Lys Gln
        670                 675                 680

TCT TTT AAA CAG ACT GGA GAG TTT GGG GAA AAA AGG AAG AAT TCT ATT             2232
Ser Phe Lys Gln Thr Gly Glu Phe Gly Glu Lys Arg Lys Asn Ser Ile
685                 690                 695                 700

CTC AAT CCA ATC AAC TCT ATA CGA AAA TTT TCC ATT GTG CAA AAG ACT             2280
Leu Asn Pro Ile Asn Ser Ile Arg Lys Phe Ser Ile Val Gln Lys Thr
                    705                 710                 715

CCC TTA CAA ATG AAT GGC ATC GAA GAG GAT TCT GAT GAG CCT TTA GAG             2328
Pro Leu Gln Met Asn Gly Ile Glu Glu Asp Ser Asp Glu Pro Leu Glu
            720                 725                 730

AGA AGG CTG TCC TTA GTA CCA GAT TCT GAG CAG GGA GAG GCG ATA CTG             2376
Arg Arg Leu Ser Leu Val Pro Asp Ser Glu Gln Gly Glu Ala Ile Leu
                735                 740                 745

CCT CGC ATC AGC GTG ATC AGC ACT GGC CCC ACG CTT CAG GCA CGA AGG             2424
Pro Arg Ile Ser Val Ile Ser Thr Gly Pro Thr Leu Gln Ala Arg Arg
        750                 755                 760

AGG CAG TCT GTC CTG AAC CTG ATG ACA CAC TCA GTT AAC CAA GGT CAG             2472
Arg Gln Ser Val Leu Asn Leu Met Thr His Ser Val Asn Gln Gly Gln
765                 770                 775                 780

AAC ATT CAC CGA AAG ACA ACA GCA TCC ACA CGA AAA GTG TCA CTG GCC             2520
Asn Ile His Arg Lys Thr Thr Ala Ser Thr Arg Lys Val Ser Leu Ala
                    785                 790                 795

CCT CAG GCA AAC TTG ACT GAA CTG GAT ATA TAT TCA AGA AGG TTA TCT             2568
Pro Gln Ala Asn Leu Thr Glu Leu Asp Ile Tyr Ser Arg Arg Leu Ser
            800                 805                 810

CAA GAA ACT GGC TTG GAA ATA AGT GAA GAA ATT AAC GAA GAA GAC TTA             2616
Gln Glu Thr Gly Leu Glu Ile Ser Glu Glu Ile Asn Glu Glu Asp Leu
                815                 820                 825

AAG GAG TGC CTT TTT GAT GAT ATG GAG AGC ATA CCA GCA GTG ACT ACA             2664
Lys Glu Cys Leu Phe Asp Asp Met Glu Ser Ile Pro Ala Val Thr Thr
        830                 835                 840

TGG AAC ACA TAC CTT CGA TAT ATT ACT GTC CAC AAG AGC TTA ATT TTT             2712
Trp Asn Thr Tyr Leu Arg Tyr Ile Thr Val His Lys Ser Leu Ile Phe
845                 850                 855                 860

GTG CTA ATT TGG TGC TTA GTA ATT TTT CTG GCA GAG GTG GCT GCT TCT             2760
Val Leu Ile Trp Cys Leu Val Ile Phe Leu Ala Glu Val Ala Ala Ser
                    865                 870                 875

TTG GTT GTG CTG TGG CTC CTT GGA AAC ACT CCT CTT CAA GAC AAA GGG             2808
Leu Val Val Leu Trp Leu Leu Gly Asn Thr Pro Leu Gln Asp Lys Gly
            880                 885                 890

AAT AGT ACT CAT AGT AGA AAT AAC AGC TAT GCA GTG ATT ATC ACC AGC             2856
```

```
                Asn Ser Thr His Ser Arg Asn Asn Ser Tyr Ala Val Ile Ile Thr Ser
                            895                 900                 905

ACC AGT TCG TAT TAT GTG TTT TAC ATT TAC GTG GGA GTA GCC GAC ACT         2904
Thr Ser Ser Tyr Tyr Val Phe Tyr Ile Tyr Val Gly Val Ala Asp Thr
910                 915                 920

TTG CTT GCT ATG GGA TTC TTC AGA GGT CTA CCA CTG GTG CAT ACT CTA         2952
Leu Leu Ala Met Gly Phe Phe Arg Gly Leu Pro Leu Val His Thr Leu
925                 930                 935                 940

ATC ACA GTG TCG AAA ATT TTA CAC CAC AAA ATG TTA CAT TCT GTT CTT         3000
Ile Thr Val Ser Lys Ile Leu His His Lys Met Leu His Ser Val Leu
                    945                 950                 955

CAA GCA CCT ATG TCA ACC CTC AAC ACG TTG AAA GCA GGT GGG ATT CTT         3048
Gln Ala Pro Met Ser Thr Leu Asn Thr Leu Lys Ala Gly Gly Ile Leu
                960                 965                 970

AAT AGA TTC TCC AAA GAT ATA GCA ATT TTG GAT GAC CTT CTG CCT CTT         3096
Asn Arg Phe Ser Lys Asp Ile Ala Ile Leu Asp Asp Leu Leu Pro Leu
            975                 980                 985

ACC ATA TTT GAC TTC ATC CAG TTG TTA TTA ATT GTG ATT GGA GCT ATA         3144
Thr Ile Phe Asp Phe Ile Gln Leu Leu Leu Ile Val Ile Gly Ala Ile
        990                 995                 1000

GCA GTT GTC GCA GTT TTA CAA CCC TAC ATC TTT GTT GCA ACA GTG CCA         3192
Ala Val Val Ala Val Leu Gln Pro Tyr Ile Phe Val Ala Thr Val Pro
1005                1010                1015                1020

GTG ATA GTG GCT TTT ATT ATG TTG AGA GCA TAT TTC CTC CAA ACC TCA         3240
Val Ile Val Ala Phe Ile Met Leu Arg Ala Tyr Phe Leu Gln Thr Ser
                1025                1030                1035

CAG CAA CTC AAA CAA CTG GAA TCT GAA GGC AGG AGT CCA ATT TTC ACT         3288
Gln Gln Leu Lys Gln Leu Glu Ser Glu Gly Arg Ser Pro Ile Phe Thr
            1040                1045                1050

CAT CTT GTT ACA AGC TTA AAA GGA CTA TGG ACA CTT CGT GCC TTC GGA         3336
His Leu Val Thr Ser Leu Lys Gly Leu Trp Thr Leu Arg Ala Phe Gly
        1055                1060                1065

CGG CAG CCT TAC TTT GAA ACT CTG TTC CAC AAA GCT CTG AAT TTA CAT         3384
Arg Gln Pro Tyr Phe Glu Thr Leu Phe His Lys Ala Leu Asn Leu His
    1070                1075                1080

ACT GCC AAC TGG TTC TTG TAC CTG TCA ACA CTG CGC TGG TTC CAA ATG         3432
Thr Ala Asn Trp Phe Leu Tyr Leu Ser Thr Leu Arg Trp Phe Gln Met
1085                1090                1095                1100

AGA ATA GAA ATG ATT TTT GTC ATC TTC TTC ATT GCT GTT ACC TTC ATT         3480
Arg Ile Glu Met Ile Phe Val Ile Phe Phe Ile Ala Val Thr Phe Ile
                1105                1110                1115

TCC ATT TTA ACA ACA GGA GAA GGA GAA GGA AGA GTT GGT ATT ATC CTG         3528
Ser Ile Leu Thr Thr Gly Glu Gly Glu Gly Arg Val Gly Ile Ile Leu
            1120                1125                1130

ACT TTA GCC ATG AAT ATC ATG AGT ACA TTG CAG TGG GCT GTA AAC TCC         3576
Thr Leu Ala Met Asn Ile Met Ser Thr Leu Gln Trp Ala Val Asn Ser
        1135                1140                1145

AGC ATA GAT GTG GAT AGC TTG ATG CGA TCT GTG AGC CGA GTC TTT AAG         3624
Ser Ile Asp Val Asp Ser Leu Met Arg Ser Val Ser Arg Val Phe Lys
    1150                1155                1160

TTC ATT GAC ATG CCA ACA GAA GGT AAA CCT ACC AAG TCA ACC AAA CCA         3672
Phe Ile Asp Met Pro Thr Glu Gly Lys Pro Thr Lys Ser Thr Lys Pro
1165                1170                1175                1180

TAC AAG AAT GGC CAA CTC TCG AAA GTT ATG ATT ATT GAG AAT TCA CAC         3720
Tyr Lys Asn Gly Gln Leu Ser Lys Val Met Ile Ile Glu Asn Ser His
                1185                1190                1195

GTG AAG AAA GAT GAC ATC TGG CCC TCA GGG GGC CAA ATG ACT GTC AAA         3768
Val Lys Lys Asp Asp Ile Trp Pro Ser Gly Gly Gln Met Thr Val Lys
            1200                1205                1210

GAT CTC ACA GCA AAA TAC ACA GAA GGT GGA AAT GCC ATA TTA GAG AAC         3816
```

```
Asp Leu Thr Ala Lys Tyr Thr Glu Gly Gly Asn Ala Ile Leu Glu Asn
    1215                1220                1225

ATT TCC TTC TCA ATA AGT CCT GGC CAG AGG GTG GGC CTC TTG GGA AGA        3864
Ile Ser Phe Ser Ile Ser Pro Gly Gln Arg Val Gly Leu Leu Gly Arg
        1230                1235                1240

ACT GGA TCA GGG AAG AGT ACT TTG TTA TCA GCT TTT TTG AGA CTA CTG        3912
Thr Gly Ser Gly Lys Ser Thr Leu Leu Ser Ala Phe Leu Arg Leu Leu
1245                1250                1255                1260

AAC ACT GAA GGA GAA ATC CAG ATC GAT GGT GTG TCT TGG GAT TCA ATA        3960
Asn Thr Glu Gly Glu Ile Gln Ile Asp Gly Val Ser Trp Asp Ser Ile
                1265                1270                1275

ACT TTG CAA CAG TGG AGG AAA GCC TTT GGA GTG ATA CCA CAG AAA GTA        4008
Thr Leu Gln Gln Trp Arg Lys Ala Phe Gly Val Ile Pro Gln Lys Val
            1280                1285                1290

TTT ATT TTT TCT GGA ACA TTT AGA AAA AAC TTG GAT CCC TAT GAA CAG        4056
Phe Ile Phe Ser Gly Thr Phe Arg Lys Asn Leu Asp Pro Tyr Glu Gln
        1295                1300                1305

TGG AGT GAT CAA GAA ATA TGG AAA GTT GCA GAT GAG GTT GGG CTC AGA        4104
Trp Ser Asp Gln Glu Ile Trp Lys Val Ala Asp Glu Val Gly Leu Arg
    1310                1315                1320

TCT GTG ATA GAA CAG TTT CCT GGG AAG CTT GAC TTT GTC CTT GTG GAT        4152
Ser Val Ile Glu Gln Phe Pro Gly Lys Leu Asp Phe Val Leu Val Asp
1325                1330                1335                1340

GGG GGC TGT GTC CTA AGC CAT GGC CAC AAG CAG TTG ATG TGC TTG GCT        4200
Gly Gly Cys Val Leu Ser His Gly His Lys Gln Leu Met Cys Leu Ala
                1345                1350                1355

AGA TCT GTT CTC AGT AAG GCG AAG ATC TTG CTG CTT GAT GAA CCC AGT        4248
Arg Ser Val Leu Ser Lys Ala Lys Ile Leu Leu Leu Asp Glu Pro Ser
            1360                1365                1370

GCT CAT TTG GAT CCA GTA ACA TAC CAA ATA ATT AGA AGA ACT CTA AAA        4296
Ala His Leu Asp Pro Val Thr Tyr Gln Ile Ile Arg Arg Thr Leu Lys
        1375                1380                1385

CAA GCA TTT GCT GAT TGC ACA GTA ATT CTC TGT GAA CAC AGG ATA GAA        4344
Gln Ala Phe Ala Asp Cys Thr Val Ile Leu Cys Glu His Arg Ile Glu
    1390                1395                1400

GCA ATG CTG GAA TGC CAA CAA TTT TTG GTC ATA GAA GAG AAC AAA GTG        4392
Ala Met Leu Glu Cys Gln Gln Phe Leu Val Ile Glu Glu Asn Lys Val
1405                1410                1415                1420

CGG CAG TAC GAT TCC ATC CAG AAA CTG CTG AAC GAG AGG AGC CTC TTC        4440
Arg Gln Tyr Asp Ser Ile Gln Lys Leu Leu Asn Glu Arg Ser Leu Phe
                1425                1430                1435

CGG CAA GCC ATC AGC CCC TCC GAC AGG GTG AAG CTC TTT CCC CAC CGG        4488
Arg Gln Ala Ile Ser Pro Ser Asp Arg Val Lys Leu Phe Pro His Arg
            1440                1445                1450

AAC TCA AGC AAG TGC AAG TCT AAG CCC CAG ATT GCT GCT CTG AAA GAG        4536
Asn Ser Ser Lys Cys Lys Ser Lys Pro Gln Ile Ala Ala Leu Lys Glu
        1455                1460                1465

GAG ACA GAA GAA GAG GTG CAA GAT ACA AGG CTT TAGAGAGCAG CATAAATGTT     4589
Glu Thr Glu Glu Glu Val Gln Asp Thr Arg Leu
    1470                1475

GACATGGGAC ATTTGCTCAT GGAATTGGAG CTCGTGGGAC AGTCACCTCA TGGAATTGGA     4649

GCTCGTGGAA CAGTTACCTC TGCCTCAGAA ACAAGGATG AATTAAGTTT TTTTTTAAAA      4709

AAGAAACATT TGGTAAGGGG AATTGAGGAC ACTGATATGG GTCTTGATAA ATGGCTTCCT     4769

GGCAATAGTC AAATTGTGTG AAAGGTACTT CAAATCCTTG AAGATTTACC ACTTGTGTTT     4829

TGCAAGCCAG ATTTTCCTGA AAACCCTTGC CATGTGCTAG TAATTGGAAA GGCAGCTCTA     4889

AATGTCAATC AGCCTAGTTG ATCAGCTTAT TGTCTAGTGA AACTCGTTAA TTTGTAGTGT     4949

TGGAGAAGAA CTGAAAATCAT ACTTCTTAGG GTTATGATTA AGTAATGATA ACTGGAAACT    5009
```

```
TCAGCGGTTT ATATAAGCTT GTATTCCTTT TTCTCTCCTC TCCCCATGAT GTTTAGAAAC    5069

ACAACTATAT TGTTTGCTAA GCATTCCAAC TATCTCATTT CCAAGCAAGT ATTAGAATAC    5129

CACAGGAACC ACAAGACTGC ACATCAAAAT ATGCCCCATT CAACATCTAG TGAGCAGTCA    5189

GGAAAGAGAA CTTCCAGATC CTGGAAATCA GGGTTAGTAT TGTCCAGGTC TACCAAAAAT    5249

CTCAATATTT CAGATAATCA CAATACATCC CTTACCTGGG AAAGGGCTGT TATAATCTTT    5309

CACAGGGGAC AGGATGGTTC CCTTGATGAA GAAGTTGATA TGCCTTTTCC CAACTCCAGA    5369

AAGTGACAAG CTCACAGACC TTTGAACTAG AGTTTAGCTG GAAAAGTATG TTAGTGCAAA    5429

TTGTCACAGG ACAGCCCTTC TTTCCACAGA AGCTCCAGGT AGAGGGTGTG TAAGTAGATA    5489

GGCCATGGGC ACTGTGGGTA GACACACATG AAGTCCAAGC ATTTAGATGT ATAGGTTGAT    5549

GGTGGTATGT TTTCAGGCTA GATGTATGTA CTTCATGCTG TCTACACTAA GAGAGAATGA    5609

GAGACACACT GAAGAAGCAC CAATCATGAA TTAGTTTTAT ATGCTTCTGT TTTATAATTT    5669

TGTGAAGCAA AATTTTTTCT CTAGGAAATA TTTATTTTAA TAATGTTTCA AACATATATT    5729

ACAATGCTGT ATTTTAAAAG AATGATTATG AATTACATTT GTATAAAATA ATTTTTATAT    5789

TTGAAATATT GACTTTTTAT GGCACTAGTA TTTTTATGAA ATATTATGTT AAAACTGGGA    5849

CAGGGGAGAA CCTAGGGTGA TATTAACCAG GGGCCATGAA TCACCTTTTG GTCTGGAGGG    5909

AAGCCTTGGG GCTGATCGAG TTGTTGCCCA CAGCTGTATG ATTCCCAGCC AGACACAGCC    5969

TCTTAGATGC AGTTCTGAAG AAGATGGTAC CACCAGTCTG ACTGTTTCCA TCAAGGGTAC    6029

ACTGCCTTCT CAACTCCAAA CTGACTCTTA AGAAGACTGC ATTATATTTA TTACTGTAAG    6089

AAAATATCAC TTGTCAATAA AATCCATACA TTTGTGT                             6126

(2) INFORMATION FOR SEQ ID NO:4:

(i) SEQUENCE CHARACTERISTICS:
        (A) LENGTH: 1479 amino acids
        (B) TYPE: amino acid
        (D) TOPOLOGY: linear (ii) MOLECULE TYPE: protein (xi) SEQUENCE DESCRIPTION: SEQ ID NO:4:

Met Gln Arg Ser Pro Leu Glu Lys Ala Ser Val Ser Lys Leu Phe
 1               5                  10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160
```

```
Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Gly Val Ser Tyr Asp
            500                 505                 510

Glu Tyr Arg Tyr Arg Ser Val Ile Lys Ala Cys Gln Leu Glu Glu Asp
        515                 520                 525

Ile Ser Lys Phe Ala Glu Lys Asp Asn Ile Val Leu Gly Glu Gly Gly
    530                 535                 540

Ile Thr Leu Ser Gly Gly Gln Arg Ala Arg Ile Ser Leu Ala Arg Ala
545                 550                 555                 560

Val Tyr Lys Asp Ala Asp Leu Tyr Leu Leu Asp Ser Pro Phe Gly Tyr
                565                 570                 575

Leu Asp Val Leu Thr Glu Lys Glu Ile Phe Glu Ser Cys Val Cys Lys
```

```
                   580             585             590
Leu Met Ala Asn Lys Thr Arg Ile Leu Val Thr Ser Lys Met Glu His
            595             600             605
Leu Lys Lys Ala Asp Lys Ile Leu Ile Leu Asn Glu Gly Ser Ser Tyr
610             615             620
Phe Tyr Gly Thr Phe Ser Glu Leu Gln Asn Leu Gln Pro Asp Phe Ser
625             630             635             640
Ser Lys Leu Met Gly Cys Asp Ser Phe Asp Gln Phe Ser Ala Glu Arg
                645             650             655
Arg Asn Ser Ile Leu Thr Glu Thr Leu His Arg Phe Ser Leu Glu Gly
            660             665             670
Asp Ala Pro Val Ser Trp Thr Glu Thr Lys Lys Gln Ser Phe Lys Gln
        675             680             685
Thr Gly Glu Phe Gly Glu Lys Arg Lys Asn Ser Ile Leu Asn Pro Ile
690             695             700
Asn Ser Ile Arg Lys Phe Ser Ile Val Gln Lys Thr Pro Leu Gln Met
705             710             715             720
Asn Gly Ile Glu Glu Asp Ser Asp Glu Pro Leu Glu Arg Arg Leu Ser
                725             730             735
Leu Val Pro Asp Ser Glu Gln Gly Glu Ala Ile Leu Pro Arg Ile Ser
            740             745             750
Val Ile Ser Thr Gly Pro Thr Leu Gln Ala Arg Arg Arg Gln Ser Val
        755             760             765
Leu Asn Leu Met Thr His Ser Val Asn Gln Gly Gln Asn Ile His Arg
        770             775             780
Lys Thr Thr Ala Ser Thr Arg Lys Val Ser Leu Ala Pro Gln Ala Asn
785             790             795             800
Leu Thr Glu Leu Asp Ile Tyr Ser Arg Arg Leu Ser Gln Glu Thr Gly
            805             810             815
Leu Glu Ile Ser Glu Glu Ile Asn Glu Glu Asp Leu Lys Glu Cys Leu
            820             825             830
Phe Asp Asp Met Glu Ser Ile Pro Ala Val Thr Thr Trp Asn Thr Tyr
            835             840             845
Leu Arg Tyr Ile Thr Val His Lys Ser Leu Ile Phe Val Leu Ile Trp
        850             855             860
Cys Leu Val Ile Phe Leu Ala Glu Val Ala Ala Ser Leu Val Val Leu
865             870             875             880
Trp Leu Leu Gly Asn Thr Pro Leu Gln Asp Lys Gly Asn Ser Thr His
            885             890             895
Ser Arg Asn Asn Ser Tyr Ala Val Ile Ile Thr Ser Thr Ser Ser Tyr
            900             905             910
Tyr Val Phe Tyr Ile Tyr Val Gly Val Ala Asp Thr Leu Leu Ala Met
        915             920             925
Gly Phe Phe Arg Gly Leu Pro Leu Val His Thr Leu Ile Thr Val Ser
930             935             940
Lys Ile Leu His His Lys Met Leu His Ser Val Leu Gln Ala Pro Met
945             950             955             960
Ser Thr Leu Asn Thr Leu Lys Ala Gly Gly Ile Leu Asn Arg Phe Ser
                965             970             975
Lys Asp Ile Ala Ile Leu Asp Asp Leu Leu Pro Leu Thr Ile Phe Asp
            980             985             990
Phe Ile Gln Leu Leu Leu Ile Val Ile Gly Ala Ile Ala Val Val Ala
        995             1000            1005
```

-continued

```
Val Leu Gln Pro Tyr Ile Phe Val Ala Thr Val Pro Val Ile Val Ala
    1010                1015                1020

Phe Ile Met Leu Arg Ala Tyr Phe Leu Gln Thr Ser Gln Gln Leu Lys
1025                1030                1035                1040

Gln Leu Glu Ser Glu Gly Arg Ser Pro Ile Phe Thr His Leu Val Thr
            1045                1050                1055

Ser Leu Lys Gly Leu Trp Thr Leu Arg Ala Phe Gly Arg Gln Pro Tyr
            1060                1065                1070

Phe Glu Thr Leu Phe His Lys Ala Leu Asn Leu His Thr Ala Asn Trp
            1075                1080                1085

Phe Leu Tyr Leu Ser Thr Leu Arg Trp Phe Gln Met Arg Ile Glu Met
            1090                1095                1100

Ile Phe Val Ile Phe Phe Ile Ala Val Thr Phe Ile Ser Ile Leu Thr
1105                1110                1115                1120

Thr Gly Glu Gly Glu Gly Arg Val Gly Ile Ile Leu Thr Leu Ala Met
            1125                1130                1135

Asn Ile Met Ser Thr Leu Gln Trp Ala Val Asn Ser Ser Ile Asp Val
            1140                1145                1150

Asp Ser Leu Met Arg Ser Val Ser Arg Val Phe Lys Phe Ile Asp Met
            1155                1160                1165

Pro Thr Glu Gly Lys Pro Thr Lys Ser Thr Lys Pro Tyr Lys Asn Gly
            1170                1175                1180

Gln Leu Ser Lys Val Met Ile Ile Glu Asn Ser His Val Lys Lys Asp
1185                1190                1195                1200

Asp Ile Trp Pro Ser Gly Gly Gln Met Thr Val Lys Asp Leu Thr Ala
            1205                1210                1215

Lys Tyr Thr Glu Gly Gly Asn Ala Ile Leu Glu Asn Ile Ser Phe Ser
            1220                1225                1230

Ile Ser Pro Gly Gln Arg Val Gly Leu Leu Gly Arg Thr Gly Ser Gly
            1235                1240                1245

Lys Ser Thr Leu Leu Ser Ala Phe Leu Arg Leu Leu Asn Thr Glu Gly
            1250                1255                1260

Glu Ile Gln Ile Asp Gly Val Ser Trp Asp Ser Ile Thr Leu Gln Gln
1265                1270                1275                1280

Trp Arg Lys Ala Phe Gly Val Ile Pro Gln Lys Val Phe Ile Phe Ser
            1285                1290                1295

Gly Thr Phe Arg Lys Asn Leu Asp Pro Tyr Glu Gln Trp Ser Asp Gln
            1300                1305                1310

Glu Ile Trp Lys Val Ala Asp Glu Val Gly Leu Arg Ser Val Ile Glu
            1315                1320                1325

Gln Phe Pro Gly Lys Leu Asp Phe Val Leu Val Asp Gly Gly Cys Val
            1330                1335                1340

Leu Ser His Gly His Lys Gln Leu Met Cys Leu Ala Arg Ser Val Leu
1345                1350                1355                1360

Ser Lys Ala Lys Ile Leu Leu Leu Asp Glu Pro Ser Ala His Leu Asp
            1365                1370                1375

Pro Val Thr Tyr Gln Ile Ile Arg Arg Thr Leu Lys Gln Ala Phe Ala
            1380                1385                1390

Asp Cys Thr Val Ile Leu Cys Glu His Arg Ile Glu Ala Met Leu Glu
            1395                1400                1405

Cys Gln Gln Phe Leu Val Ile Glu Glu Asn Lys Val Arg Gln Tyr Asp
            1410                1415                1420

Ser Ile Gln Lys Leu Leu Asn Glu Arg Ser Leu Phe Arg Gln Ala Ile
1425                1430                1435                1440
```

-continued

Ser Pro Ser Asp Arg Val Lys Leu Phe Pro His Arg Asn Ser Ser Lys
            1445                1450                1455

Cys Lys Ser Lys Pro Gln Ile Ala Ala Leu Lys Glu Glu Thr Glu Glu
        1460                1465                1470

Glu Val Gln Asp Thr Arg Leu
    1475

(2) INFORMATION FOR SEQ ID NO:5:

(i) SEQUENCE CHARACTERISTICS:
        (A) LENGTH: 6129 base pairs
        (B) TYPE: nucleic acid
        (C) STRANDEDNESS: single
        (D) TOPOLOGY: linear (xi) SEQUENCE DESCRIPTION: SEQ ID NO:5:

| | | | | | |
|---|---|---|---|---|---|
| AATTGGAAGC | AAATGACATC | ACAGCAGGTC | AGAGAAAAAG | GGTTGAGCGG | CAGGCACCCA | 60 |
| GAGTAGTAGG | TCTTTGGCAT | TAGGAGCTTG | AGCCCAGACG | GCCCTAGCAG | GGACCCCAGC | 120 |
| GCCCGAGAGA | CCATGCAGAG | GTCGCCTCTG | GAAAAGGCCA | GCGTTGTCTC | CAAACTTTTT | 180 |
| TTCAGCTGGA | CCAGACCAAT | TTTGAGGAAA | GGATACAGAC | AGCGCCTGGA | ATTGTCAGAC | 240 |
| ATATACCAAA | TCCCTTCTGT | TGATTCTGCT | GACAATCTAT | CTGAAAAATT | GGAAAGAGAA | 300 |
| TGGGATAGAG | AGCTGGCTTC | AAAGAAAAAT | CCTAAACTCA | TTAATGCCCT | TCGGCGATGT | 360 |
| TTTTTCTGGA | GATTTATGTT | CTATGGAATC | TTTTTATATT | TAGGGAAGT | CACCAAAGCA | 420 |
| GTACAGCCTC | TCTTACTGGG | AAGAATCATA | GCTTCCTATG | ACCCGGATAA | CAAGGAGGAA | 480 |
| CGCTCTATCG | CGATTTATCT | AGGCATAGGC | TTATGCCTTC | TCTTTATTGT | GAGGACACTG | 540 |
| CTCCTACACC | CAGCCATTTT | TGGCCTTCAT | CACATTGGAA | TGCAGATGAG | AATAGCTATG | 600 |
| TTTAGTTTGA | TTTATAAGAA | GACTTTAAAG | CTGTCAAGCC | GTGTTCTAGA | TAAAATAAGT | 660 |
| ATTGGACAAC | TTGTTAGTCT | CCTTTCCAAC | AACCTGAACA | AATTTGATGA | AGGACTTGCA | 720 |
| TTGGCACATT | TCGTGTGGAT | CGCTCCTTTG | CAAGTGGCAC | TCCTCATGGG | GCTAATCTGG | 780 |
| GAGTTGTTAC | AGGCGTCTGC | CTTCTGTGGA | CTTGGTTTCC | TGATAGTCCT | TGCCCTTTTT | 840 |
| CAGGCTGGGC | TAGGGAGAAT | GATGATGAAG | TACAGAGATC | AGAGAGCTGG | GAAGATCAGT | 900 |
| GAAAGACTTG | TGATTACCTC | AGAAATGATT | GAAAATATCC | AATCTGTTAA | GGCATACTGC | 960 |
| TGGGAAGAAG | CAATGGAAAA | AATGATTGAA | AACTTAAGAC | AAACAGAACT | GAAACTGACT | 1020 |
| CGGAAGGCAG | CCTATGTGAG | ATACTTCAAT | AGCTCAGCCT | TCTTCTTCTC | AGGGTTCTTT | 1080 |
| GTGGTGTTTT | TATCTGTGCT | TCCCTATGCA | CTAATCAAAG | GAATCATCCT | CCGGAAAATA | 1140 |
| TTCACCACCA | TCTCATTCTG | CATTGTTCTG | CGCATGGCGG | TCACTCGGCA | ATTTCCCTGG | 1200 |
| GCTGTACAAA | CATGGTATGA | CTCTCTTGGA | GCAATAAACA | AAATACAGGA | TTTCTTACAA | 1260 |
| AAGCAAGAAT | ATAAGACATT | GGAATATAAC | TTAACGACTA | CAGAAGTAGT | GATGGAGAAT | 1320 |
| GTAACAGCCT | TCTGGGAGGA | GGGATTTGGG | GAATTATTTG | AGAAAGCAAA | ACAAAACAAT | 1380 |
| AACAATAGAA | AAACTTCTAA | TGGTGATGAC | AGCCTCTTCT | TCAGTAATTT | CTCACTTCTT | 1440 |
| GGTACTCCTG | TCCTGAAAGA | TATTAATTTC | AAGATAGAAA | GAGGACAGTT | GTTGGCGGTT | 1500 |
| GCTGGATCCA | CTGGAGCAGG | CAAGACTTCA | CTTCTAATGA | TGATTATGGG | AGAACTGGAG | 1560 |
| CCTTCAGAGG | GTAAAATTAA | GCACAGTGGA | AGAATTTCAT | TCTGTTCTCA | GTTTTCCTGG | 1620 |
| ATTATGCCTG | GCACCATTAA | AGAAAATATC | ATCTTTGGTG | TTTCCTATGA | TGAATATAGA | 1680 |
| TACAGAAGCG | TCATCAAAGC | ATGCCAACTA | GAAGAGGACA | TCTCCAAGTT | TGCAGAGAAA | 1740 |
| GACAATATAG | TTCTTGGAGA | AGGTGGAATC | ACACTGAGTG | GAGAYCAACG | AGCAAGAATT | 1800 |

```
TCTTTAGCAA GAGCAGTATA CAAAGATGCT GATTTGTATT TATTAGACTC TCCTTTTGGA    1860

TACCTAGATG TTTTAACAGA AAAAGAAATA TTTGAAAGCT GTGTCTGTAA ACTGATGGCT    1920

AACAAAACTA GGATTTTGGT CACTTCTAAA ATGGAACATT TAAAGAAAGC TGACAAAATA    1980

TTAATTTTGA ATGAAGGTAG CAGCTATTTT TATGGGACAT TTTCAGAACT CCAAAATCTA    2040

CAGCCAGACT TTAGCTCAAA ACTCATGGGA TGTGATTCTT TCGACCAATT TAGTGCAGAA    2100

AGAAGAAATT CAATCCTAAC TGAGACCTTA CACCGTTTCT CATTAGAAGG AGATGCTCCT    2160

GTCTCCTGGA CAGAAACAAA AAAACAATCT TTTAAACAGA CTGGAGAGTT TGGGAAAAA     2220

AGGAAGAATT CTATTCTCAA TCCAATCAAC TCTATACGAA AATTTTCCAT TGTGCAAAAG    2280

ACTCCCTTAC AAATGAATGG CATCGAAGAG GATTCTGATG AGCCTTTAGA GAGAAGGCTG    2340

TCCTTAGTAC CAGATTCTGA GCAGGGAGAG GCGATACTGC CTCGCATCAG CGTGATCAGC    2400

ACTGGCCCCA CGCTTCAGGC ACGAAGGAGG CAGTCTGTCC TGAACCTGAT GACACACTCA    2460

GTTAACCAAG GTCAGAACAT TCACCGAAAG ACAACAGCAT CCACACGAAA AGTGTCACTG    2520

GCCCCTCAGG CAAACTTGAC TGAACTGGAT ATATATTCAA GAAGGTTATC TCAAGAAACT    2580

GGCTTGGAAA TAAGTGAAGA AATTAACGAA GAAGACTTAA AGGAGTGCCT TTTTGATGAT    2640

ATGGAGAGCA TACCAGCAGT GACTACATGG AACACATACC TTCGATATAT TACTGTCCAC    2700

AAGAGCTTAA TTTTTGTGCT AATTTGGTGC TTAGTAATTT TTCTGGCAGA GGTGGCTGCT    2760

TCTTTGGTTG TGCTGTGGCT CCTTGGAAAC ACTCCTCTTC AAGACAAAGG GAATAGTACT    2820

CATAGTAGAA ATAACAGCTA TGCAGTGATT ATCACCAGCA CCAGTTCGTA TTATGTGTTT    2880

TACATTTACG TGGGAGTAGC CGACACTTTG CTTGCTATGG GATTCTTCAG AGGTCTACCA    2940

CTGGTGCATA CTCTAATCAC AGTGTCGAAA ATTTTACACC ACAAAATGTT ACATTCTGTT    3000

CTTCAAGCAC CTATGTCAAC CCTCAACACG TTGAAAGCAG GTGGGATTCT TAATAGATTC    3060

TCCAAAGATA TAGCAATTTT GGATGACCTT CTGCCTCTTA CCATATTTGA CTTCATCCAG    3120

TTGTTATTAA TTGTGATTGG AGCTATAGCA GTTGTCGCAG TTTTACAACC CTACATCTTT    3180

GTTGCAACAG TGCCAGTGAT AGTGGCTTTT ATTATGTTGA GAGCATATTT CCTCCAAACC    3240

TCACAGCAAC TCAAACAACT GGAATCTGAA GGCAGGAGTC CAATTTTCAC TCATCTTGTT    3300

ACAAGCTTAA AAGGACTATG GACACTTCGT GCCTTCGGAC GGCAGCCTTA CTTTGAAACT    3360

CTGTTCCACA AAGCTCTGAA TTTACATACT GCCAACTGGT TCTTGTACCT GTCAACACTG    3420

CGCTGGTTCC AAATGAGAAT AGAAATGATT TTTGTCATCT TCTTCATTGC TGTTACCTTC    3480

ATTTCCATTT TAACAACAGG AGAAGGAGAA GGAAGAGTTG GTATTATCCT GACTTTAGCC    3540

ATGAATATCA TGAGTACATT GCAGTGGGCT GTAAACTCCA GCATAGATGT GGATAGCTTG    3600

ATGCGATCTG TGAGCCGAGT CTTTAAGTTC ATTGACATGC CAACAGAAGG TAAACCTACC    3660

AAGTCAACCA AACCATACAA GAATGGCCAA CTCTCGAAAG TTATGATTAT TGAGAATTCA    3720

CACGTGAAGA AGATGACAT CTGGCCCTCA GGGGGCCAAA TGACTGTCAA AGATCTCACA    3780

GCAAAATACA CAGAAGGTGG AAATGCCATA TTAGAGAACA TTTCCTTCTC AATAAGTCCT    3840

GGCCAGAGGG TGGGCCTCTT GGGAAGAACT GGATCAGGGA AGAGTACTTT GTTATCAGCT    3900

TTTTTGAGAC TACTGAACAC TGAAGGAGAA ATCCAGATCG ATGGTGTGTC TTGGGATTCA    3960

ATAACTTTGC AACAGTGGAG AAAAGCCTTT GGAGTGATAC CACAGAAAGT ATTTATTTTT    4020

TCTGGAACAT TTAGAAAAAA CTTGGATCCC TATGAACAGT GGAGTGATCA AGAAATATGG    4080

AAAGTTGCAG ATGAGGTTGG GCTCAGATCT GTGATAGAAC AGTTTCCTGG GAAGCTTGAC    4140

TTTGTCCTTG TGGATGGGGG CTGTGTCCTA AGCCATGGCC ACAAGCAGTT GATGTGCTTG    4200
```

```
GCTAGATCTG TTCTCAGTAA GGCGAAGATC TTGCTGCTTG ATGAACCCAG TGCTCATTTG    4260

GATCCAGTAA CATACCAAAT AATTAGAAGA ACTCTAAAAC AAGCATTTGC TGATTGCACA    4320

GTAATTCTCT GTGAACACAG GATAGAAGCA ATGCTGGAAT GCCAACAATT TTTGGTCATA    4380

GAAGAGAACA AAGTGCGGCA GTACGATTCC ATCCAGAAAC TGCTGAACGA GAGGAGCCTC    4440

TTCCGGCAAG CCATCAGCCC CTCCGACAGG GTGAAGCTCT TTCCCCACCG GAACTCAAGC    4500

AAGTGCAAGT CTAAGCCCCA GATTGCTGCT CTGAAAGAGG AGACAGAAGA AGAGGTGCAA    4560

GATACAAGGC TTTAGAGAGC AGCATAAATG TTGACATGGG ACATTTGCTC ATGGAATTGG    4620

AGCTCGTGGG ACAGTCACCT CATGGAATTG GAGCTCGTGG AACAGTTACC TCTGCCTCAG    4680

AAAACAAGGA TGAATTAAGT TTTTTTTTAA AAAGAAACA TTTGGTAAGG GGAATTGAGG    4740

ACACTGATAT GGGTCTTGAT AAATGGCTTC CTGGCAATAG TCAAATTGTG TGAAAGGTAC    4800

TTCAAATCCT TGAAGATTTA CCACTTGTGT TTTGCAAGCC AGATTTTCCT GAAAACCCTT    4860

GCCATGTGCT AGTAATTGGA AAGGCAGCTC TAAATGTCAA TCAGCCTAGT TGATCAGCTT    4920

ATTGTCTAGT GAAACTCGTT AATTTGTAGT GTTGGAGAAG AACTGAAATC ATACTTCTTA    4980

GGGTTATGAT TAAGTAATGA TAACTGGAAA CTTCAGCGGT TTATATAAGC TTGTATTCCT    5040

TTTTCTCTCC TCTCCCCATG ATGTTTAGAA ACACAACTAT ATTGTTTGCT AAGCATTCCA    5100

ACTATCTCAT TTCCAAGCAA GTATTAGAAT ACCACAGGAA CCACAAGACT GCACATCAAA    5160

ATATGCCCCA TTCAACATCT AGTGAGCAGT CAGGAAAGAG AACTTCCAGA TCCTGGAAAT    5220

CAGGGTTAGT ATTGTCCAGG TCTACCAAAA ATCTCAATAT TTCAGATAAT CACAATACAT    5280

CCCTTACCTG GGAAAGGGCT GTTATAATCT TTCACAGGGG ACAGGATGGT TCCCTTGATG    5340

AAGAAGTTGA TATGCCTTTT CCCAACTCCA GAAAGTGACA AGCTCACAGA CCTTTGAACT    5400

AGAGTTTAGC TGGAAAAGTA TGTTAGTGCA AATTGTCACA GGACAGCCCT TCTTTCCACA    5460

GAAGCTCCAG GTAGAGGGTG TGTAAGTAGA TAGGCCATGG GCACTGTGGG TAGACACACA    5520

TGAAGTCCAA GCATTTAGAT GTATAGGTTG ATGGTGGTAT GTTTTCAGGC TAGATGTATG    5580

TACTTCATGC TGTCTACACT AAGAGAGAAT GAGAGACACA CTGAAGAAGC ACCAATCATG    5640

AATTAGTTTT ATATGCTTCT GTTTTATAAT TTTGTGAAGC AAAATTTTTT CTCTAGGAAA    5700

TATTTATTTT AATAATGTTT CAAACATATA TTACAATGCT GTATTTTAAA AGAATGATTA    5760

TGAATTACAT TTGTATAAAA TAATTTTTAT ATTTGAAATA TTGACTTTTT ATGGCACTAG    5820

TATTTTTATG AAATATTATG TTAAAACTGG GACAGGGGAG AACCTAGGGT GATATTAACC    5880

AGGGGCCATG AATCACCTTT TGGTCTGGAG GGAAGCCTTG GGGCTGATCG AGTTGTTGCC    5940

CACAGCTGTA TGATTCCCAG CCAGACACAG CCTCTTAGAT GCAGTTCTGA AGAAGATGGT    6000

ACCACCAGTC TGACTGTTTC CATCAAGGGT ACACTGCCTT CTCAACTCCA AACTGACTCT    6060

TAAGAAGACT GCATTATATT TATTACTGTA AGAAAATATC ACTTGTCAAT AAAATCCATA    6120

CATTTGTGT                                                           6129
```

(2) INFORMATION FOR SEQ ID NO:6:

(i) SEQUENCE CHARACTERISTICS:
        (A) LENGTH: 1480 amino acids
        (B) TYPE: amino acid
        (C) STRANDEDNESS:
        (D) TOPOLOGY: linear (xi) SEQUENCE DESCRIPTION: SEQ ID NO:6:

```
Met Gln Arg Ser Pro Leu Glu Lys Ala Ser Val Val Ser Lys Leu Phe
1               5                   10                  15
```

```
Phe Ser Trp Thr Arg Pro Ile Leu Arg Lys Gly Tyr Arg Gln Arg Leu
             20                  25                  30

Glu Leu Ser Asp Ile Tyr Gln Ile Pro Ser Val Asp Ser Ala Asp Asn
             35                  40                  45

Leu Ser Glu Lys Leu Glu Arg Glu Trp Asp Arg Glu Leu Ala Ser Lys
 50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
             100                 105                 110

Asn Lys Glu Glu Arg Ser Ile Ala Ile Tyr Leu Gly Ile Gly Leu Cys
             115                 120                 125

Leu Leu Phe Ile Val Arg Thr Leu Leu Leu His Pro Ala Ile Phe Gly
             130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                 165                 170                 175

Ile Gly Gln Leu Val Ser Leu Leu Ser Asn Asn Leu Asn Lys Phe Asp
             180                 185                 190

Glu Gly Leu Ala Leu Ala His Phe Val Trp Ile Ala Pro Leu Gln Val
             195                 200                 205

Ala Leu Leu Met Gly Leu Ile Trp Glu Leu Leu Gln Ala Ser Ala Phe
 210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                 245                 250                 255

Glu Arg Leu Val Ile Thr Ser Glu Met Ile Glu Asn Ile Gln Ser Val
             260                 265                 270

Lys Ala Tyr Cys Trp Glu Glu Ala Met Glu Lys Met Ile Glu Asn Leu
             275                 280                 285

Arg Gln Thr Glu Leu Lys Leu Thr Arg Lys Ala Ala Tyr Val Arg Tyr
 290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                 325                 330                 335

Phe Thr Thr Ile Ser Phe Cys Ile Val Leu Arg Met Ala Val Thr Arg
             340                 345                 350

Gln Phe Pro Trp Ala Val Gln Thr Trp Tyr Asp Ser Leu Gly Ala Ile
             355                 360                 365

Asn Lys Ile Gln Asp Phe Leu Gln Lys Gln Glu Tyr Lys Thr Leu Glu
 370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                 405                 410                 415

Asn Asn Arg Lys Thr Ser Asn Gly Asp Asp Ser Leu Phe Phe Ser Asn
             420                 425                 430

Phe Ser Leu Leu Gly Thr Pro Val Leu Lys Asp Ile Asn Phe Lys Ile
```

-continued

```
                435                 440                 445
Glu Arg Gly Gln Leu Leu Ala Val Ala Gly Ser Thr Gly Ala Gly Lys
    450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
                500                 505                 510
Asp Glu Tyr Arg Tyr Arg Ser Val Ile Lys Ala Cys Gln Leu Glu Glu
                515                 520                 525
Asp Ile Ser Lys Phe Ala Glu Lys Asp Asn Ile Val Leu Gly Glu Gly
                530                 535                 540
Gly Ile Thr Leu Ser Gly Asp Gln Arg Ala Arg Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
                580                 585                 590
Lys Leu Met Ala Asn Lys Thr Arg Ile Leu Val Thr Ser Lys Met Glu
                595                 600                 605
His Leu Lys Lys Ala Asp Lys Ile Leu Ile Leu Asn Glu Gly Ser Ser
610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
                660                 665                 670
Gly Asp Ala Pro Val Ser Trp Thr Glu Thr Lys Lys Gln Ser Phe Lys
                675                 680                 685
Gln Thr Gly Glu Phe Gly Glu Lys Arg Lys Asn Ser Ile Leu Asn Pro
    690                 695                 700
Ile Asn Ser Ile Arg Lys Phe Ser Ile Val Gln Lys Thr Pro Leu Gln
705                 710                 715                 720
Met Asn Gly Ile Glu Glu Asp Ser Asp Glu Pro Leu Glu Arg Arg Leu
                725                 730                 735
Ser Leu Val Pro Asp Ser Glu Gln Gly Glu Ala Ile Leu Pro Arg Ile
                740                 745                 750
Ser Val Ile Ser Thr Gly Pro Thr Leu Gln Ala Arg Arg Arg Gln Ser
                755                 760                 765
Val Leu Asn Leu Met Thr His Ser Val Asn Gln Gly Gln Asn Ile His
770                 775                 780
Arg Lys Thr Thr Ala Ser Thr Arg Lys Val Ser Leu Ala Pro Gln Ala
785                 790                 795                 800
Asn Leu Thr Glu Leu Asp Ile Tyr Ser Arg Arg Leu Ser Gln Glu Thr
                805                 810                 815
Gly Leu Glu Ile Ser Glu Glu Ile Asn Glu Glu Asp Leu Lys Glu Cys
                820                 825                 830
Leu Phe Asp Asp Met Glu Ser Ile Pro Ala Val Thr Thr Trp Asn Thr
                835                 840                 845
Tyr Leu Arg Tyr Ile Thr Val His Lys Ser Leu Ile Phe Val Leu Ile
                850                 855                 860
```

```
Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
            885                 890                 895

His Ser Arg Asn Asn Ser Tyr Ala Val Ile Ile Thr Ser Thr Ser Ser
        900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
        995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
            1060                1065                1070

Tyr Phe Glu Thr Leu Phe His Lys Ala Leu Asn Leu His Thr Ala Asn
        1075                1080                1085

Trp Phe Leu Tyr Leu Ser Thr Leu Arg Trp Phe Gln Met Arg Ile Glu
    1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
                1125                1130                1135

Met Asn Ile Met Ser Thr Leu Gln Trp Ala Val Asn Ser Ser Ile Asp
            1140                1145                1150

Val Asp Ser Leu Met Arg Ser Val Ser Arg Val Phe Lys Phe Ile Asp
        1155                1160                1165

Met Pro Thr Glu Gly Lys Pro Thr Lys Ser Thr Lys Pro Tyr Lys Asn
    1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
                1205                1210                1215

Ala Lys Tyr Thr Glu Gly Gly Asn Ala Ile Leu Glu Asn Ile Ser Phe
            1220                1225                1230

Ser Ile Ser Pro Gly Gln Arg Val Gly Leu Leu Gly Arg Thr Gly Ser
        1235                1240                1245

Gly Lys Ser Thr Leu Leu Ser Ala Phe Leu Arg Leu Leu Asn Thr Glu
    1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
                1285                1290                1295
```

```
Ser Gly Thr Phe Arg Lys Asn Leu Asp Pro Tyr Glu Gln Trp Ser Asp
            1300                1305                1310

Gln Glu Ile Trp Lys Val Ala Asp Glu Val Gly Leu Arg Ser Val Ile
        1315                1320                1325

Glu Gln Phe Pro Gly Lys Leu Asp Phe Val Leu Val Asp Gly Gly Cys
    1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
                1365                1370                1375

Asp Pro Val Thr Tyr Gln Ile Ile Arg Arg Thr Leu Lys Gln Ala Phe
            1380                1385                1390

Ala Asp Cys Thr Val Ile Leu Cys Glu His Arg Ile Glu Ala Met Leu
            1395                1400                1405

Glu Cys Gln Gln Phe Leu Val Ile Glu Glu Asn Lys Val Arg Gln Tyr
    1410                1415                1420

Asp Ser Ile Gln Lys Leu Leu Asn Glu Arg Ser Leu Phe Arg Gln Ala
1425                1430                1435                1440

Ile Ser Pro Ser Asp Arg Val Lys Leu Phe Pro His Arg Asn Ser Ser
                1445                1450                1455

Lys Cys Lys Ser Lys Pro Gln Ile Ala Ala Leu Lys Glu Glu Thr Glu
            1460                1465                1470

Glu Glu Val Gln Asp Thr Arg Leu
            1475                1480
```